United States Patent
Berry et al.

(10) Patent No.: US 9,034,571 B2
(45) Date of Patent: May 19, 2015

(54) THREE-DIMENSIONAL, PREVASCULARIZED, ENGINEERED TISSUE CONSTRUCTS, METHODS OF MAKING AND METHODS OF USING THE TISSUE CONSTRUCTS

(71) Applicants: The UAB Research Foundation, Birmingham, AL (US); Southern Research Institute, Birmingham, AL (US)

(72) Inventors: Joel L. Berry, Birmingham, AL (US); Timothy M. Wick, Homewood, AL (US); Joanne Murphy-Ullrich, Birmingham, AL (US); Andrew D. Penman, Birmingham, AL (US); Andrew W. Cain, Birmingham, AL (US); Andra Rixse Frost, Birmingham, AL (US)

(73) Assignees: THE UAB RESEARCH FOUNDATION, Birmingham, AL (US); SOUTHERN RESEARCH INSTITUTE, Birmingham, AL (US)

( * ) Notice: Subject to any disclaimer, the term of this patent is extended or adjusted under 35 U.S.C. 154(b) by 0 days.

(21) Appl. No.: 13/786,903

(22) Filed: Mar. 6, 2013

(65) Prior Publication Data
US 2013/0236879 A1    Sep. 12, 2013

Related U.S. Application Data

(60) Provisional application No. 61/607,397, filed on Mar. 6, 2012.

(51) Int. Cl.
*C12N 5/07* (2010.01)
*C12N 5/071* (2010.01)
*G01N 33/50* (2006.01)
*C12M 3/00* (2006.01)
*C12M 3/06* (2006.01)

(52) U.S. Cl.
CPC ........ *G01N 33/5088* (2013.01); *G01N 33/5011* (2013.01); *G01N 33/5064* (2013.01); *C12M 21/08* (2013.01); *C12M 23/16* (2013.01)

(58) Field of Classification Search
CPC ... C12M 25/14; C12N 5/0062; C12N 5/0691; C12N 2513/00; A61K 2035/12; A61K 49/0004; A61K 35/13; G01N 2500/10
See application file for complete search history.

(56) References Cited

U.S. PATENT DOCUMENTS

| | | |
|---|---|---|
| 2003/0049839 A1 | 3/2003 | Romero-Ortega et al. |
| 2008/0300691 A1 | 12/2008 | Romero-Ortega et al. |
| 2010/0075293 A1 | 3/2010 | Chang et al. |
| 2010/0136114 A1 | 6/2010 | Mao |
| 2011/0020950 A1 | 1/2011 | Vogel et al. |
| 2011/0201669 A1* | 8/2011 | Cao .............................. 514/44 A |

OTHER PUBLICATIONS

Huh, D. et al. 2011. From 3D cell culture to organs-on-chips. Trends in Cell Biology 21(12):745-754. specif. pp. 745-750.*
Drury, J.L. et al. 2003.Hydrogels for tissue engineering: scaffold design variables and applications. Biomaterials 24: 4337-4351. specif. pp. 4337-4339.*
Pec, M.K. et al. 2010. Reticulated vitreous carbon: a useful material for cell adhesion and tissue invasion. European Cells and Materials 20: 282-294. specif. p. 282.*
The International Search Report and Written Opinion dated Jun. 21, 2013.

* cited by examiner

*Primary Examiner* — John S Brusca
*Assistant Examiner* — Sharon M. Papciak
(74) *Attorney, Agent, or Firm* — Thomas Horstemeyer, LLP

(57) ABSTRACT

Three-dimensional (3D), prevascularized, engineered tissue constructs, 3D prevascularized engineered tissue models of cancer, and bioreactors and bioreactor arrays including the tissue constructs are disclosed. Methods of making the tissue constructs, methods of using the tissue constructs, methods of drug discovery using the tissue constructs and/or cancer models, and the like are also disclosed.

23 Claims, 12 Drawing Sheets

THREE-DIMENSIONAL, PREVASCULARIZED, ENGINEERED TISSUE CONSTRUCTS, METHODS OF MAKING AND METHODS OF USING THE TISSUE CONSTRUCTS

CROSS-REFERENCE TO RELATED APPLICATION

This application claims priority to U.S. provisional application entitled, "PREVASCULARIZED 3D CO-CULTURED MODEL FOR BREAST CANCER DRUG DEVELOPMENT," having Ser. No. 61/607,397 filed on Mar. 6, 2012, which is entirely incorporated herein by reference.

BACKGROUND

Current drug development platforms such as two-dimensional (2D) in vitro cell culture systems and in vivo animal studies do not accurately predict human in vivo effectiveness of candidate therapeutics. These cell culture systems have limited similarities to primary human cells and tissues as only one cell type is employed, and animal studies have a generally limited ability to recapitulate human drug response as different species have differences in metabolism, physiology, and behavior. Many experimental drugs fail in clinical studies due to the inability of current screening technologies, such as in vitro laboratory tissue analysis and animal studies, to accurately predict how the drugs will behave in people.

Therefore, the drug discovery and development fields need an in vitro platform to test candidate therapeutics for better predictions of human response. Current in vitro systems (e.g., rotating bioreactors, suspension of spheroids, and growth on a porous scaffold) are limited in size (1-2 mm) and tend to be two dimensional. Attempts at 3D tissue constructs have had only limited success and have been very small or had a short life-span. The failure of these tissue models are due, at least in part, to the absence of a model vascular system to allow diffusion of oxygen and nutrients into the tissue to support more substantial, natural, sustained, tissue growth.

SUMMARY

Embodiments of the present disclosure provide for three-dimensional (3D) prevascularized engineered tissue constructs, 3D prevascularized engineered tissue models for cancer, perfusion bioreactors including the tissue constructs, methods of making the tissue constructs, methods of using the tissue constructs, methods of drug discovery using the tissue constructs, and the like.

An embodiment of a three-dimensional (3D), engineered, vascularized tissue construct of the present disclosure includes a 3D, biocompatible scaffold material; a 3D network of living cells within the scaffold material; a plurality of microchannels extending through the construct, such that a substantial portion of the channels have an inlet at one surface of the construct and an outlet at an opposing surface of the construct, and where the channels form a lumen for allowing passage of liquid through the construct; and a plurality of endothelial cells at least partially lining the lumen.

The present disclosure also provides embodiments of a 3D vascularized biocompatible scaffold for supporting in vitro, 3D tissue culture including a 3D, biocompatible scaffold material comprising a solid, porous material, a gel matrix material, or a combination of these materials. The solid, porous material is chosen from the group of materials including: aerogels, reticulate vitreous carbon, particle stabilized foam, and combinations of these materials, and the gel matrix material is chosen from the group of gel matrix materials including: synthetic hydrogels, naturally-derived hydrogels, and combinations of these materials. The 3D vascularized biocompatible scaffold also includes a plurality of channels extending through the scaffold, such that a substantial portion of the channels have an inlet at one surface of the scaffold and an outlet at an opposing surface of the scaffold, and where the channels form lumen for allowing passage of liquid through the scaffold. In embodiments of the 3D, vascularized, biocompatible scaffold, the gel matrix material includes one or more hydrogels selected from the group of synthetic and naturally derived hydrogels including: collagen, fibrin, Matrigel™, bacterial cellulose, HuBiogel™, alginate, polymer based hydrogels, copolymer based hydrogels, polyethylene glycol (PEG) based hydrogels, elastin, and keratin. Also, in embodiments, the 3D vascularized biocompatible scaffold of the present disclosure includes a porous, material selected from the group including: aerogels, particle stabilized biocompatible foams, reticulate vitreous carbon (RVC), natural electrospun polymers, synthetic electrospun polymers, and combinations of these materials. In embodiments of the 3D, vascularized tissue constructs and scaffolds of the present disclosure, the microchannels have a diameter of about 200 to about 450 microns. In some embodiments, the microchannels have a diameter of about 250 microns or less.

Embodiments of the present disclosure also include three-dimensional (3D), in vitro, vascularized cancer models including a 3D tissue construct of the present disclosure. In embodiments the 3D tissue construct of the cancer model includes a biocompatible scaffold material; a 3D network of living cells within the scaffold material, where the network of cells includes cancer cells or a combination of cancer cells and non-cancerous cells; a plurality of channels extending through the construct, such that a substantial portion of the channels have an inlet at one surface of the construct and an outlet at an opposing surface of the construct, where the channels form a lumen for allowing passage of fluid media through the construct; and a plurality of endothelial cells at least partially lining the lumen. In embodiments of the 3D vascularized cancer model of the present disclosure, the model is a human breast cancer model and the network of living cells includes human breast cancer tumor cells and non-cancerous human breast fibroblast cells.

The present disclosure also includes perfusion bioreactors including the 3D engineered tissue constructs of the present disclosure. In an embodiment, perfusion bioreactors of the present disclosure include a three-dimensional (3D), engineered tissue construct of the present disclosure as described above and a tissue chamber configured to house the tissue construct such that the tissue construct forms a barrier between upstream and downstream flow of media through the chamber, directing flow of media through the channels of the tissue construct. In embodiments, the chamber has at least one input portal upstream of the location of the tissue construct, at least one output portal downstream of the location of the tissue construct, and at least one pump to control flow of media through the tissue chamber. As described above, in embodiments, the 3D engineered tissue constructs for use in the bioreactor include a 3D, biocompatible scaffold material; a 3D network of living cells within the scaffold material; a plurality of channels extending through the construct, such that a substantial portion of the channels have an inlet at one surface of the construct and an outlet at an opposing surface of the construct, where the channels form lumen for allowing passage of fluid media through the construct; and a plurality of endothelial cells at least partially lining the lumen.

The present disclosure also provides methods of making a three-dimensional (3D), vascularized, tissue construct in vitro. In embodiments, methods of making the 3D vascularized tissue construct include providing a 3D vascularized biocompatible scaffold, where the scaffold includes a 3D, biocompatible scaffold material and a plurality of channels extending through the scaffold, such that a substantial portion of the channels have an inlet at one surface of the scaffold and an outlet at an opposing surface of the scaffold, forming lumen for allowing passage of liquid through the scaffold. The methods also include seeding the lumen with endothelial cells, such that endothelial cells line at least a portion of the lumen and seeding the scaffold with cells of at least one tissue type. The methods further include perfusing the scaffold with cell culture media, and incubating the seeded scaffold, such that a 3D network of cells of the at least one tissue type grows within the scaffold.

Methods of the present disclosure also include methods of making a three-dimensional (3D), vascularized scaffolding material of the present disclosure. In embodiments, such methods include
providing a 3D, biocompatible scaffold material and forming a plurality of microchannels in the scaffold material with a microchannel construct, where the channels extend through the scaffold, such that a substantial portion of the channels have an inlet at one surface of the scaffold and an outlet at an opposing surface of the scaffold, forming lumen for allowing passage of liquid through the scaffold.

The present disclosure also includes methods of screening a test compound including providing a three-dimensional (3D), engineered, vascularized tissue construct of the present disclosure, exposing the 3D tissue construct to the test compound; and monitoring any changes in the tissue construct after exposure to the test compound, where the changes are selected from the group including: histological, biochemical, and physiological changes, or a combination thereof. In embodiments, the screening methods of the present disclosure include methods of screening a potential cancer therapeutic compound. In embodiments, such methods include providing a 3D, engineered, vascularized cancer tissue construct of the present disclosure where the 3D network of living cells within the scaffold material includes cancer cells or a combination of cancer cells and non-cancerous cells, exposing the 3D cancer tissue construct to a test compound; and detecting changes in growth or viability of the cancer cell network after exposure to the test compound, where a decrease in growth or viability of the cancer cells indicates the test compound is a potential breast cancer therapeutic compound. In embodiments such methods also include detecting toxicity of the cancer therapeutic compound as measured by one or more of histological, biochemical, physiological changes, of the cell network.

The present disclosure also includes bioreactor networks including an array of interconnected bioreactors and at least one pump to control flow of media through the bioreactors, where the bioreactors in the array are in fluid communication with each other. In embodiments of the bioreactor networks, at least one bioreactor in the array contains cells from a different tissue type than the cells in at least one other bioreactor in the array. In embodiments of the bioreactor networks, each bioreactor includes: a three-dimensional (3D), engineered tissue construct of the present disclosure and a tissue chamber configured to house the tissue construct such that the tissue construct forms a barrier between upstream and downstream flow of media through the chamber directing flow of media through the channels of the tissue construct, where the chamber has at least one input portal upstream of the location of the tissue construct and at least one output portal downstream of the location of the tissue construct.

These embodiments, uses of these embodiments, and other uses, features and advantages of the present disclosure, will become more apparent to those of ordinary skill in the relevant art when the following detailed description of the preferred embodiments is read in conjunction with the appended figures.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3A shows an exploded view of the bioreactor, while FIG. 3B shows a view of the assembled bioreactor.

FIG. 4A shows a side view of an assembled bioreactor, and FIG. 4B shows a top view of an open bioreactor.

FIG. 5 shows an image of a 250 micron diameter channel within an embodiment of a construct of the present disclosure with bacterial cellulose as the scaffold material. Scale bar is 30 microns.

FIG. 13A shows cells at day 11 grown on an aerogel substrate (such as described below in Example 3). Cell adhesion is visible on the inside of individual pores of the scaffolding material. FIG. 13B shows MDA-MB-231 cells grown on RVC 65 at day 11.

FIG. 14A shows an image of a 45 ppi collagen/RVC scaffold (1.5 mg/ml collagen/RVC) with two 400 micron diameter microchannels shown penetrating through the 4 mm thick RVC/collagen scaffold. FIG. 14B shows an image of a 45 ppi collagen/Matrigel/RVC scaffold (1.9 mg/ml collagen/Matrigel/RVC) with three 400 micron diameter micro-channels through the scaffold. FIG. 14C is an image of a section (100 um) through a collagen/RVC/Matrigel scaffold material; the microchannels are visible as clear areas, and portions of the RVC scaffolding material are visible as the black portions. FIG. 14D is an image of a section (20 um) through gel material illustrating endothelial cells lining the lumen of the microchannels.

DETAILED DESCRIPTION

Figure 1:
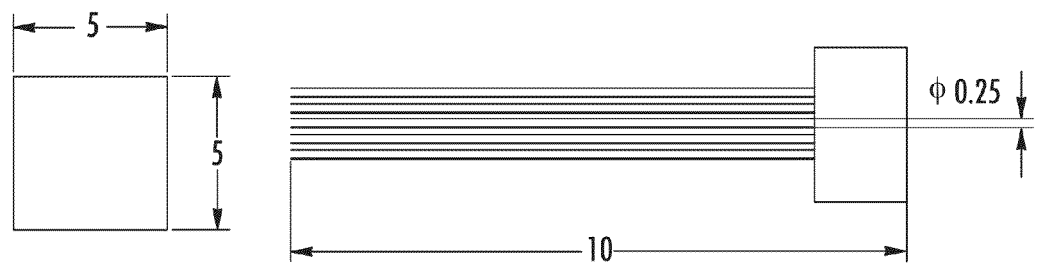
FIG. 1 is a schematic illustration of an embodiment of a micro-channel construct for forming micro-channels in a 3D construct of the present disclosure.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, organic chemistry, organometallic chemistry, polymer chemistry, microbiology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

As used herein, the term "engineered" indicates that the engineered object is created and/or altered by man. An engineered object may include naturally derived substances, but the object itself is altered in some way by human intervention and design.

The term "vascularized" as used herein, indicates that an object includes conduits (e.g., vessels, channels, tubes) capable of transporting fluids (e.g., culture media, cells in liquid media, nutrients, etc.) through the object/construct.

As used herein the term "channels" or "microchannels" refers to tube-like formations within a construct. The channels have a generally cylindrical shape, with a generally circular cross-section. The channels have an open (e.g., hollow or substantially hollow) interior (referred to herein as a "lumen") creating a via/conduit for the transport of fluids. Microchannels, as used herein, have a diameter in the micron range (e.g., 100-900 microns, 200-500 microns, etc.).

As used herein the term "biocompatible" refers to the ability to co-exist with a living biological substance and/or biological system (e.g., a cell, cellular components, living tissue, organ, etc.) without exerting undue stress, toxicity, or adverse effects on the biological substance or system.

The term "biocompatible scaffold material" refers to any compound substance with sufficient structural stability to provide a substrate to support the growth of a living biological substance (e.g., living cells). In embodiments of the present disclosure the biocompatible scaffold material has a three-dimensional structure (rather than a planer, 2-dimensional structure) to support three-dimensional growth of living cells.

The term "gel matrix material" refers to several different types of semi-solid to solid materials with a gel-like consistency and a structure capable of supporting the growth of living biological substances (e.g., living cells). Both synthetic and naturally derived gel matrix materials exist and are in use by those of skill in the art. Gel matrix materials include hydrogels, such as biocompatible naturally derived or synthetic hydrogels, such as, but not limited to polymer based hydrogels, PEG based hydrogels, cellulose, keratin, elastin, collagen, and the like. Gel matrix materials also include biocompatible polymer or copolymer based gel materials, such a polymer and copolymer based hydrogels. Gel matrix materials may also include a gelling agent or crosslinking agent (e.g., formaldehyde, glutaraldehyde, etc.) to increase the structural stability of the gel (e.g., to give it more "solid" characteristics).

As used herein, the phrase "solid, porous materials" refers to a scaffolding material that has a solid (rather than gel-like) consistency and has an open or porous structure in order to provide a structural framework for supporting the growth of 3D networks of living cells that has a more rigid support than a gel matrix material such as a hydrogel. In embodiments, these solid, porous materials for use in the scaffolding materials and constructs of the present disclosure are inert materials that do not interfere or exert adverse effects on biological materials grown within/on their framework. In embodiments, the solid, porous materials of the present disclosure can have a lattice-like structure that provides ample surface area to support three-dimensional cell growth. Examples of solid, porous materials that can be included in embodiments of the present disclosure are described in the discussion below.

The term "networks of cells" refers to a grouping of a plurality of cells (e.g., three or more) that are connected to each other or otherwise in cellular communication with each other. The term "3D network of cells" includes a network of cells as described above where the cells occupy three dimensional space. In other words, the three or more cells are grouped together in more than one plane.

The term "cancer", as used herein, shall be given its ordinary meaning, as a general term for diseases in which abnormal cells divide without control and form cancer or neoplastic cells or tissues. The term cancer can include cancer cells and/or precancerous cells. In particular, and in the context of the embodiments of the present disclosure, cancer refers to angiogenesis-related cancer. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor may be formed. Generally, a solid tumor is an abnormal mass of tissue that usually does not contain cysts or liquid areas (although some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult.

Benign tumors have less of a tendency to invade and are less likely to metastasize. Brain tumors spread extensively within the brain but do not usually metastasize outside the brain. Gliomas are very invasive inside the brain, even crossing hemispheres. They do divide in an uncontrolled manner, though. Depending on their location, they can be just as life threatening as malignant lesions. An example of this would be a benign tumor in the brain, which can grow and occupy space within the skull, leading to increased pressure on the brain.

It should be noted that precancerous cells, cancer, tumors are often used interchangeably in the disclosure.

The term "polymer" includes any compound that is made up of two or more monomeric units covalently bonded to each other, where the monomeric units may be the same or different, such that the polymer may be a homopolymer or a heteropolymer. Representative polymers include polyamides, such as polypeptides, poly-N-substituted glycines (polypeptoids), polysaccharides, polyethylene glycol or polyethylene oxide, plastics (e.g., poly-L-lactic acid, poly-L-glutamic acid and co-polymers thereof), nucleic acids and the like, where the polymers may be naturally occurring, non-naturally occurring, or synthetic. The term "bio-polymer" refers to a polymer made of biologically-derived and/or biologically compatible compounds The term "attached" or the phrases "interacts with" and "associated with" refers to a stable physical, biological, biochemical, and/or chemical association. In general, association can be chemical bonding (e.g., covalently or ionically), a biological interaction, a biochemical interaction, and in some instances a physical interaction. The association can be a covalent bond, a non-covalent bond, an ionic bond, a metal ion chelation interaction, as well as moieties being linked through interactions such as, but not limited to, hydrophobic interactions, hydrophilic interactions such as hydrogel bonding, charge-charge interactions, π-stacking interactions, combinations thereof, and like interactions.

Discussion

The present disclosure provides three-dimensional (3D), engineered, vascularized tissue constructs, bioreactors including the constructs, methods of making the constructs, and various methods of employing the constructs for tissue design, drug discovery, and many other uses. The 3D engineered, vascularized tissue constructs of the present disclosure represent custom-built, microphysiological platforms that support long-term tissue growth, recapitulate physiological tissue function, provide a model of human disease progression or response to external challenge (drug or pathogen), among other advantages over current technologies.

Current drug discovery platforms use 2D cell culture systems to replicate the tissue microenvironment and physiologic endpoints. 3D tissue models using primary human cells better replicate the biochemical and biophysical characteristics of the tissue. In addition, the gene expression profiles of 3D cultures more accurately mimic the native tissues and more accurately reproduce drug sensitivity responses as compared to 2D culture. At present, many 3D tissue models are developed using synthetic (hydrogel, alginate) or animal-derived (Matrigel™, HuBiogel™, collagen) biomatrix scaffolds. Furthermore, most 3D tissue construct approaches typically only culture the primary parenchymal cell type without incorporating stromal or vascular components. In contrast, the 3D vascularized tissue constructs of the present disclosure represent more 'fully human' tissue constructs by employing a biomatrix scaffold suitable for long-term culture of the appropriate human primary cell types with parenchymal and stromal cellular components in a vascularized network to accurately mimic tissue function and response to drugs.

A network of microchannels engineered within the tissue constructs of the present disclosure provides vascularization to the construct to overcome oxygen diffusion limitations in larger tissues and allows introduction of cyclic mechanical stimulation for providing proper endothelial function and metabolic communication with surrounding tissue. The vascularization of the tissue construct allows for better three-dimensional growth and growth on a larger scale with longer sustainability. These advances in 3D tissue model technology will accelerate drug development by providing tissue constructs with more physiologically relevant functions and structures and, thereby, more in vivo-like metabolic and molecular predictive endpoints.

The 3D, vascularized tissue constructs of the present disclosure are compatible with various cell types, and, thus, can be used to grow tissue constructs including any different cell type that can then be employed for many different uses. For instance, both healthy and diseased cells can be grown in the physiological environment of the present 3D vascularized tissue scaffolds and can be used to mimic various disease states, organ systems, and the like. Also, human cells from donors and patients can be used in the present constructs to create physiologically relevant tissue constructs and accurate representations of disease states. Using patient cells in making a 3d vascularized tissue construct of the present disclosure can provide a platform for personalized medicine, such as by providing a personalized model for in vitro testing drug interactions with a patient's own tissue.

These 3D multicellular tissue constructs are cultured in novel microphysiological perfusion bioreactors that permit real-time non-destructive assaying of tissue function and the capacity to connect multiple organ systems (in a 'plug-and-play' design) to replicate complex organism physiology. The bioreactors of the present disclosure are engineered to integrate with sampling and optical imaging technologies to evaluate tissue-specific function and response to drug and toxin challenges. The bioreactors can be incorporated into an array, with each bioreactor supporting a tissue construct. These 'plug-and-play' platforms can be interconnected and reconfigured to include a variety of different tissues. In embodiments the 3D tissue constructs of the present disclosure can be integrated into an array system with tissue constructs of different tissue types and/or disease states to form an integrated microphysiological system for more predictive, rapid, and cost effective drug discovery, development, efficacy and toxicology testing strategies. These innovative approaches will supplant and/or enhance current approaches utilizing 2D cell cultures and animal testing regimens for drug development and validation which are expensive, have limited predictive capacity and require extensive time for completion. The 3D tissue constructs of the present disclosure and integrated arrays of the tissue constructs will provide powerful new paradigms for more cost effective and timely translation of drugs from bench to bedside.

Embodiments of the 3D vascularized tissue constructs of the present disclosure, disease state models using the tissue constructs, bioreactors for growth and maintenance of the tissue constructs, bioreactor arrays, methods of screening test compounds using the tissue constructs, and methods of making the tissue constructs of the present disclosure and other embodiments of the present disclosure are described in greater detail below.

3D Engineered, Vascularized Tissue Constructs

The 3D engineered, vascularized tissue constructs of the present disclosure include a three-dimensional, biocompatible scaffold material for providing structural support for cell growth; a three-dimensional network of living cells within the scaffold material; a plurality of microchannels extending through the construct, where the microchannels are at least partially lined on the inner surface (lumen) with endothelial cells. The present disclosure includes both the 3D vascularized tissue constructs as well as 3D vascularized scaffolds for supporting tissue growth (e.g., pre-seeded scaffolds without the network of living cells).

Biocompatible Scaffold Material:

In order to support growth of cells in three-dimensional space, the tissue constructs of the present disclosure provide a biocompatible scaffolding material that provides structural support and integrity to the construct. In embodiments the biocompatible scaffolding material is a gel matrix material, a solid porous material, or a combination of both of these materials.

The use of gel matrix materials for use in tissue engineering and lab-on-a-chip designs is well known. In embodiments of the constructs of the present disclosure any such biocompatible gel matrix materials used in these applications can be used to provide the structural scaffolding of the present disclosure. Representative gel matrix materials include, but are not limited to synthetic and naturally-derived hydrogels. The gel matrix material of the present disclosure can include synthetic hydrogels, naturally-derived hydrogels, and combinations of both synthetic and natural hydrogels. Such hydrogels are well known in the art and can be tailored to have various physical properties (e.g., by incorporation of various polymer materials) and can be enhanced with nutrients and other proteins (e.g., growth factors). While not intending to limit the scope of this disclosure, some aspects of hydrogels and representative hydrogels are discussed below.

Generally described, a hydrogel is a natural or synthetic network of polymer chains that are hydrophilic, with water as the dispersion medium. Hydrogels are highly absorbent (they can contain over 99.9% water) and possess a degree of flexibility very similar to natural tissue, due to their significant water content. Hydrogels can be tailored to have material properties that closely match the mechanical properties of natural tissues by controlling and optimizing their porosity and conjugated adhesion and other bio-recognition or gel crosslinking molecules.

In embodiments, hydrogels can be specifically designed via tunable material properties (e.g., gel stiffness, porosity, and degradation rate). Selection of the polypeptides that make up the hydrogel and the degree of cross-linking of the polypeptides (e.g., by addition of various crosslinking agents, gelling agents, and the like) can be used to control the material characteristics of the hydrogel. In addition, the hydrogel can be designed to control the concentration of presented bioactive substrates (e.g., adhesion substrates, protease substrates, and the like). In embodiments, the hydrogel can be a hybrid synthetic material incorporating synthetic polymers such as poly(ethylene glycol) in addition to biosynthetically derived, repetitive proteins. In some embodiments, hydrogels can be formed from protein polymers that can be crosslinked into a hydrogel using a chemical, physical, and/or biological crosslinking agent (e.g., enzymes). In some embodiments, hydrogels have been synthesized that include specific protein binding domains; thus, enabling binding of proteins useful for cell growth and maintenance, such as growth factors.

The constructs of the present disclosure can include either or both naturally-derived and synthetic hydrogels. In embodiments of the present disclosure, representative naturally-derived hydrogels include, but are not limited to: collagen, fibrin, Matrigel™, bacterial cellulose, HuBiogel™, and combinations thereof.

In embodiments of the 3D vascularized tissue constructs of the present disclosure, the gel matrix material can be naturally derived hydrogels of bacterial cellulose and/or fibrin. Bacterial cellulose and fibrin hydrogels have different chemical compositions, mechanical structures, and can support different cell types. Bacterial cellulose, a non-degradable hydrogel derived from synthesis of cellulose nanofibers by bacteria, has been shown to support vascular smooth muscle cells, endothelial cells, and osteoblasts. Fibrin gel, a degradable product of blood clotting found in mammals, has been shown to support many cell types including breast cancer cells. Fibrin also plays an important role in tissue regeneration and repair. It is the major protein component of blood clots and is made via the cleavage of the protein fibrinogen by the enzyme thrombin. Firbin can form a gel at physiological temperatures and has been used extensively in biomedical engineering applications, ranging from cardiovascular tissue engineering to wound healing endeavors.

Collagen is another natural hydrogel that can be used in the 3D vascularized tissue constructs of the present disclosure. Collagen it is the most abundant protein found in mammals and is the major component of extracellular matrix. Type I collagen is the most abundant of all the collagens and plays an important role in tissue regeneration and repair. It is commercially available as a solubilized material and has been used as a 3D matrix material in many biomedical and tissue engineering applications including orthopedic tissue engineering. Type I collagen forms a hydrogel at physiological temperatures.

Matrigel™ (BD Biosciences), is a solubilized basement membrane matrix extracted from murine tumor 30. This hydrogel is also used in many tissue engineering applications. HuBiogel™ is a hydrogel that is a human biomatrix created by Vivo Biosciences (VBI). HuBiogel is a natural extracellular matrix (ECM) including Col-I, laminin, Col-IV, Col-III, entactin, and HSPG, but lacks all major known growth factors. It is more compatible with human tissues and safe, being neither angiogenic nor mitogenic. HuBiogel promotes cell growth and differentiation via local growth factor signals and allows long-term culture on or more cell types. It is compatible with human cells and/or for growth of human tissue models.

In embodiments of the present disclosure, representative synthetic hydrogels include, but are not limited to: alginate, polyethylene glycol (PEG) based hydrogels, polymer oligo (polyethylene glycol fumarate) (OPF), other biocompatible polymer or copolymer based hydrogels, and combinations of these materials.

OPF hydrogel is a synthetic polyethylene glycol (PEG) based hydrogel. OPF is a novel hydrogel developed at Rice University and has been used as a 3D matrix for soft tissue and orthopedic tissue engineering applications 36-39. Its properties, such as non-toxicity, biocompatibility and rapid gelling make it a promising material for 3D cell culture. OPF hydrogels, other PEG based hydrogels, alginate, and other synthetic hydrogels can be used as a gel matrix for forming the biocompatible scaffolding material of the present disclosure.

In embodiments of the present disclosure where the biocompatible scaffold material includes a gel matrix material it may also include one or more crosslinking agents, gelling agents, or combinations, where such agents are capable of increasing the structural stability and/or structural integrity of the gel matrix material. Due to the high content of hydrogels, some hydrogels can have a more fluid consistency than desired in the constructs of the present disclosure. Thus, in some embodiments, gelling agents and/or crosslinking agents, or the like may be used to "solidify" or "cure" the hydrogel. In some embodiments, application of heat alone may be sufficient to gel or "cure" the hydrogel. A combination of heat application, use of gelling or crosslinking agents or other fillers may be employed in embodiments of the present disclosure to provide the desired structural integrity of the scaffolding material.

While gel matrix materials, such as hydrogels, have a history of use in tissue engineering and cell culture applications with a well-plate design or thin lab-on-a-chip technologies, they have, in the past, been unable to support the growth of a large 3D tissue construct and/or long-term maintenance. The vascularization of the construct as provided by the present disclosure overcomes some of these difficulties, allowing additional delivery of culture media, nutrients, and the like to cells to allow for more sustained and substantial tissue growth. In embodiments of the present disclosure gel matrix material alone as the scaffolding material is appropriate for embodiments of constructs for use in well-plate format, some bioreactor designs, and other embodiments. However, for some applications, additional structural integrity may be desired in the scaffolding material.

In embodiments of the 3D vascularized tissue construct of the present disclosure, the biocompatible scaffolding material can include a solid, porous, material such as, but not limited to, aerogels, particle stabilized biocompatible foams, reticulate vitreous carbon (RVC), natural electrospun polymers, synthetic electrospun polymers, and combinations of these materials. Such solid, porous materials provide a solid structural framework for supporting the growth of 3D networks of living cells. In embodiments, these solid, porous materials for use in the scaffolding materials of the constructs of the present disclosure are inert materials that do not interfere or exert adverse effects on biological materials grown within/on their framework.

Figure 7:
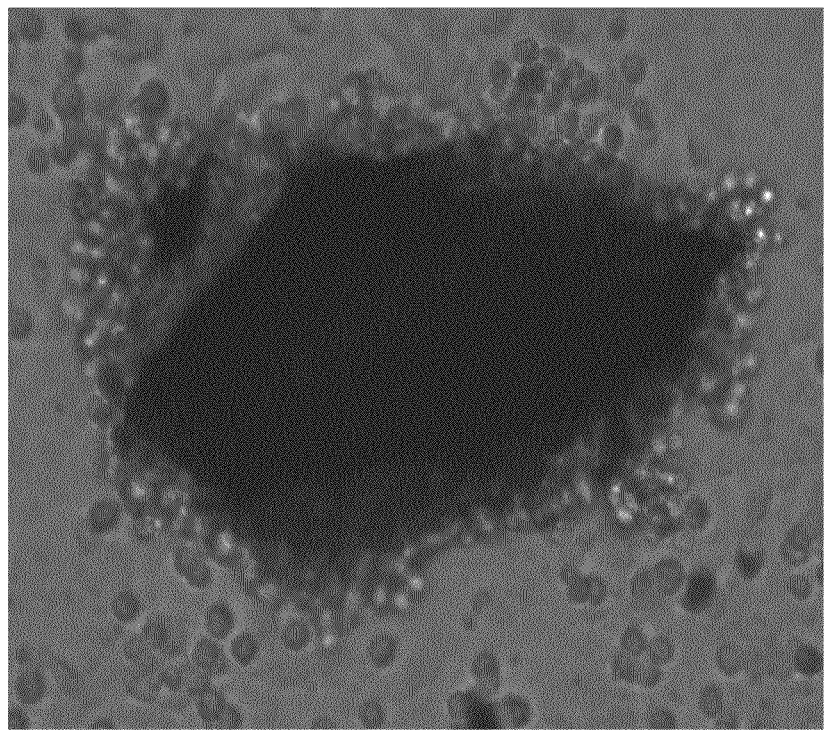
FIG. 7 is a phase contrast microscopy (PCM) image at 40× magnification illustrating MDA-MB-231 cells grown on particle stabilized foam at day 7.

Some of these solid, porous materials have a lattice-like structure that provides ample surface area to support three-dimensional cell growth. For instance, reticulate vitreous carbon (RVC) has a solid, lattice structure provided by the open pore network. An image of RVC is shown in FIG. 7. Other solid porous materials also provide a lattice-type or web-like structural features, such as aerogels, particle stabilized biocompatible foams, natural and synthetic electrospun polymers, and the like. Aerogels are solid materials derived from gels, where the liquid has been evaporated from the gel to leave an ultra-light, but strong solid framework. These materials and other biocompatible, solid, porous materials can be used alone or in combination with other materials, such as the gel matrix materials discussed above in forming the scaffolding material of the present disclosure.

Thus, in embodiments of the 3D vascularized tissue constructs and 3D vascularized scaffolding materials of the present disclosure, the biocompatible scaffold material can include one or more solid, porous materials and one or more gel matrix materials, as well as any other compounds used to enhance, modify, or control the properties of the scaffolding material (e.g., binding agents, gelling agents, cross-linking agents, proteins, polymers, and the like). In embodiments of the present disclosure, the biocompatible scaffolding material includes reticulate vitreous carbon and/or an aerogel combined with one or more gel matrix materials, such as, but not limited to, Matrigel™, bacterial cellulose, collagen, fibrin, elastin, keratin, HuBiogel, and combinations thereof. In embodiments of the present disclosure, the biocompatible scaffolding material includes RVC, Matrigel™ and collagen, as well as optional crosslinking and/or gelling agents, such as, but not limited to glutaraldehyde, formaldehyde, and the like.

Vascularization of Scaffold:

The 3D engineered vascularized tissue constructs and 3D vascularized scaffolding materials of the present disclosure include a plurality of channels extending through the construct. In embodiments, the channels are microchannels. In embodiments, the microchannels have a diameter of about 1 to about 1000 microns, from about 5 to about 600 microns, or from 200 to about 450 microns, and other ranges within and/or overlapping the stated ranges. In embodiments, the microchannels have a diameter of about 250 microns or less. In embodiments the microchannels have a diameter from about 5 to about 250 microns. The microchannels are configured such that a substantial portion of the channels have an inlet at one surface of the construct and an outlet at an opposing surface of the construct. The microchannels are substantially hollow, such that the channels form lumen for allowing passage of liquid through the construct. Thus, the microchannels create a vascular network within the scaffolding construct to facilitate the delivery of cell culture media, nutrients, oxygen, proteins, growth factors, and the like to various parts of the 3D construct, allowing for improved growth and maintenance of cells growing within the construct. In embodiments, the microchannels are substantially aligned (e.g., they are generally oriented in the same direction to allow for unidirectional flow of fluid/media through the channels).

In embodiments of the 3D vascularized constructs and scaffolding of the present disclosure, the microchannels are at least partially lined on the inner surface (lumen) with endothelial cells. These endothelial cells can form an integrated network to approximate the lining of a physiological vessel. Endothelial cells are introduced to the channels and cultured so that a plurality of endothelial cells at least partially lines the lumen. The endothelial cells can be introduced in various manners known to those of skill in the art. For instance, in an embodiment, the scaffolds/constructs having microchannels formed within the construct can be placed in culture medium containing endothelial cells and incubated for a sufficient amount of time for endothelial cell growth. In other embodiments, the endothelial cells may be seeded by perfusion with media containing the endothelial cells in a bioreactor, by a syringe pump, by injection into the microchannels or other method of delivering endothelial cells to the microchannels of the construct.

In embodiments of methods of making the constructs and scaffolds of the present disclosure, the microchannels are formed by use of a microchannel construct. In embodiments, the microchannel construct is made of a rigid, durable material, such as a metal (e.g., stainless steel), glass, polymer, resorbable filaments, and the like. The microchannel construct can have a base and an array of rods or wires for forming the microchannels. FIG. 1 represents a schematic illustration of an embodiment of a microchannel construct of the present disclosure. In embodiments of the present disclosure, the rods or wires have a generally cylindrical shape and have a cross section similar to the desired cross section of the microchannels. Thus, the rods/wires can have a diameter of about 10 to about 1000 microns, 100 to about 600 microns, about 200 to about 400 microns, and about 250 microns, and the like. In embodiments, the microchannels can also be formed by laser machining.

The microchannel construct can be used to form the channels in the 3D scaffolding material in various ways. In an embodiment where the scaffolding material includes a gel matrix material, the microchannel construct can be inserted into the gel matrix material or combination solid porous material and gel matrix material before curing (e.g. crosslinking, gelling, otherwise "solidifying") the gel matrix material. Then the microchannel construct can be removed after the gel has cured, leaving microchannels within the scaffold/construct. In other embodiments, the microchannel construct can be inserted/punched into the gel matrix, solid porous material, or combination solid porous material and gel matrix) after curing, forming or "punching" the channels into the scaffold/construct. Other methods for forming the microchannels in the construct/scaffolding may also be employed and are considered to be within the scope of the present disclosure.

3D Network of Cells:

The 3D vascularized tissue constructs of the present disclosure also include a 3D network of cells within the scaffolding material. The network of cells includes a plurality of cells growing in three-dimensional space (e.g., in more than one plane), where the cells are interconnected in some manner, such as physical contact, in cellular communication, etc. The tissue constructs of the present disclosure can support the growth of virtually any kind of cells, with animal cells being of particular interest. In embodiments, the tissue constructs of the present disclosure include mammalian cells, in particular human cells. The cells can be from any tissue of interest, including healthy and/or diseased tissue. The cells can be introduced to the scaffolding material after formation of the scaffolding material and microchannels, or, in some embodiments, contemporaneously with the addition of a gel matrix material or other agents. The cells can be introduced in culture medium, by injection, perfusion, co-incubation, or a combination of these methods and other methods known to those of skill in the art.

The tissue constructs of the present disclosure may include pathologic cells (e.g., for modeling diseased tissue), healthy cells, or a combination of healthy and pathologic cells. In general, the cell type can be a pathogenic cell that causes or is capable of causing a disease such as cancer. In an embodiment, the cell type can include a cancer cell, such as cancer human cells and/or precancerous human cells. In an embodiment, the cancer cells can include cancer cells such as metastatic cancer cells. In an embodiment, the cancer human cells can include human cancer cells such as metastatic human cancer cells. The cell types can correspond to cancers such as those defined above. In particular, the cell types can include prostate cancer cells, breast cancer cells, brain cancer cells, ovarian cancer cells, bladder cancer cell, lung cancer cells, and colon cancer cells, in humans or mammals. Although cancer and cancer cells are referred to herein, the cancer and cancer cells can be replaced with pathogenic cell.

In embodiments, the cells include a combination of cancer cells and healthy (non-cancerous) cells. In this manner, it is possible with the constructs of the present disclosure to model certain disease states in a manner similar to the in vivo state of the disease. For instance, in the case of some tumors, the 3D vascularized tissue constructs of the present disclosure allow formation of a 3D tumor in combination with healthy tissue that mimics the structure and composition of the tumor in a host. The structure provided by the scaffolding material and the vascularization provided by the microchannels allows improved growth of the cells to form tissues with a spatial orientation and structure more similar to the physiologic state.

In some embodiments of the present disclosure, the constructs can be used to provide a three dimensional (3D), in vitro, vascularized cancer model. In some such embodiments, the 3D tissue construct includes the biocompatible scaffold material with a three-dimensional network of living cells within the scaffold material, where the network of cells includes cancer cells or a combination of cancer cells and non-cancerous cells. The 3D vascularized cancer model also includes a plurality of channels extending through the construct to form lumen and a plurality of endothelial cells at least partially lining the lumen, as described above.

In embodiments, the 3D vascularized tissue construct of the present disclosure can be used to provide a model of human breast cancer. In embodiments, the 3D vascularized tissue construct includes a network of cells including breast cancer tumor cells and healthy breast tissue cells such as, but not limited to, breast fibroblast cells and/or breast epithelial cells). In some embodiments of the breast cancer model of the present disclosure, the breast cancer tumor cells form a spheroid structure. Spheroids are often formed by breast cancer cells in vivo in hosts with breast cancer. Embodiments of the present disclosure also include models of other cancers and other diseases using the 3D vascularized tissue constructs of the present disclosure.

Figure 4A:
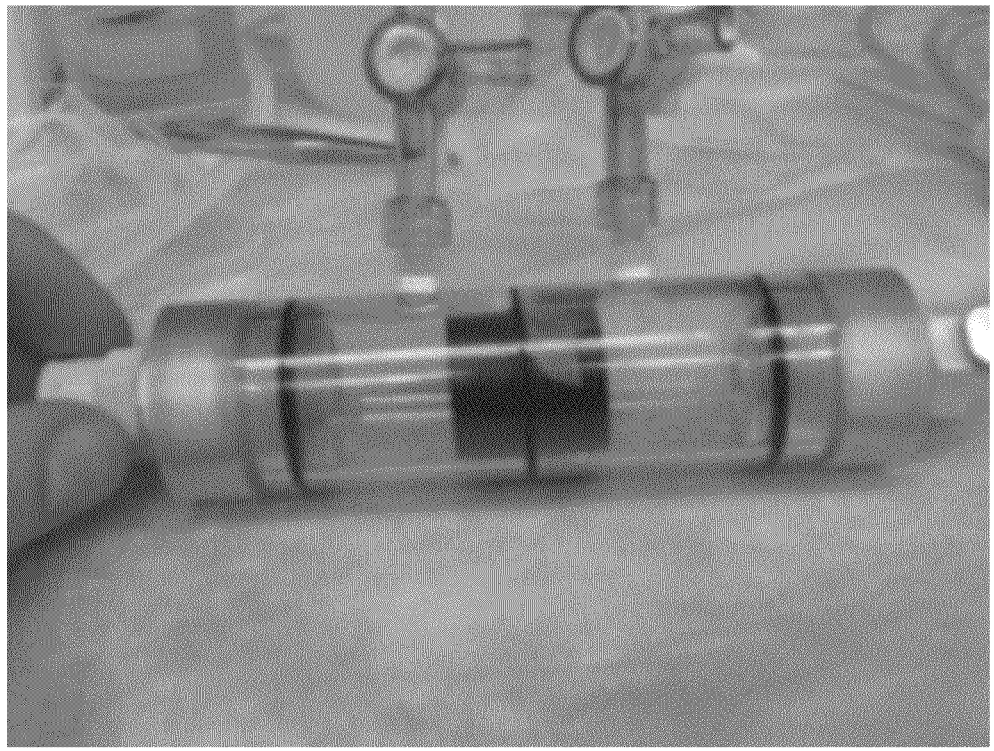
FIGS. 4A-4B are digital images representing an embodiment of a bioreactor of the present disclosure.
Figure 4B:
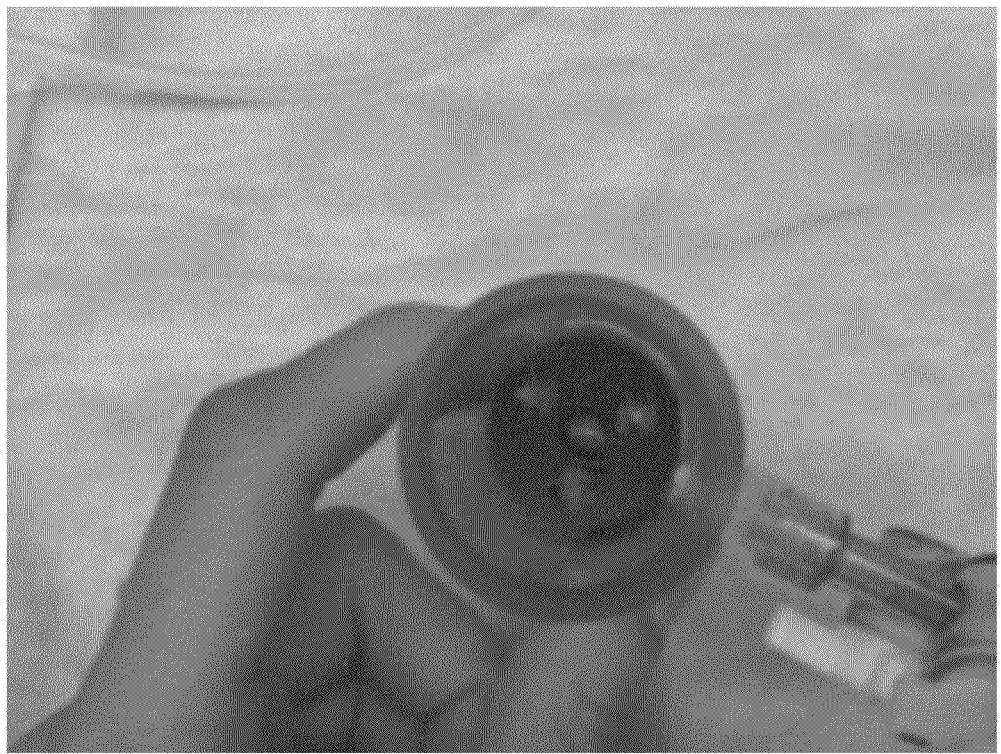
Figure 15A:
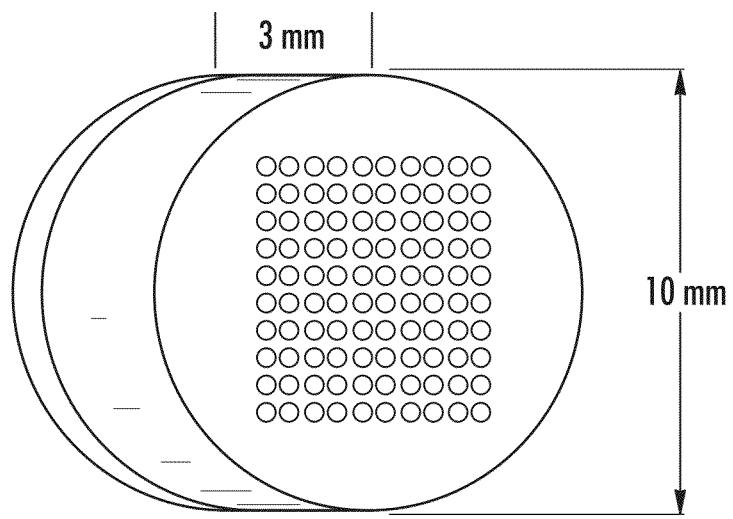
FIG. 15A is a schematic illustration of the scaffold for an embodiment of a disk shaped scaffolding of the present disclosure for an embodiment of a bioreactor of the present disclosure measuring 10 mm diameter×3 mm height (e.g., version 1 bioreactor in Example 4).
Figure 15B:
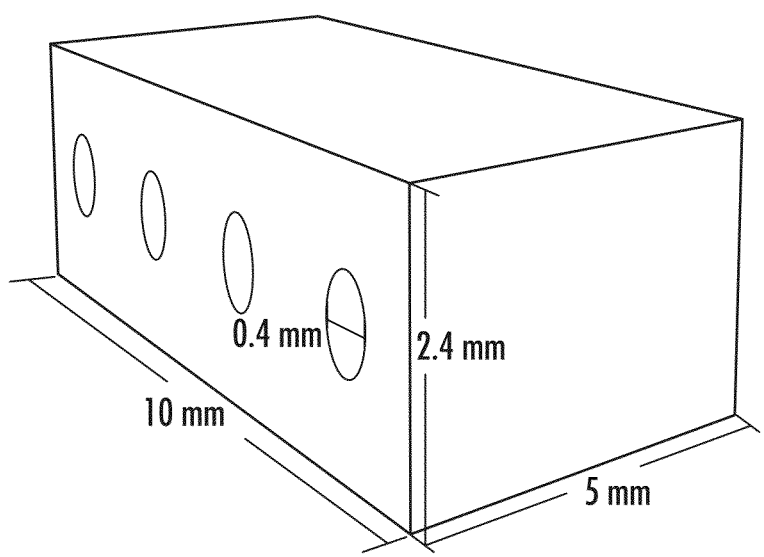
FIG. 15B is a schematic illustration of an embodiment of a rectangular-shaped scaffold for another embodiment of a bioreactor of the present disclosure measuring 10 mm width×5 mm length×2.4 mm height. (e.g., version 2 bioreactor in Example 4).
Figure 16:
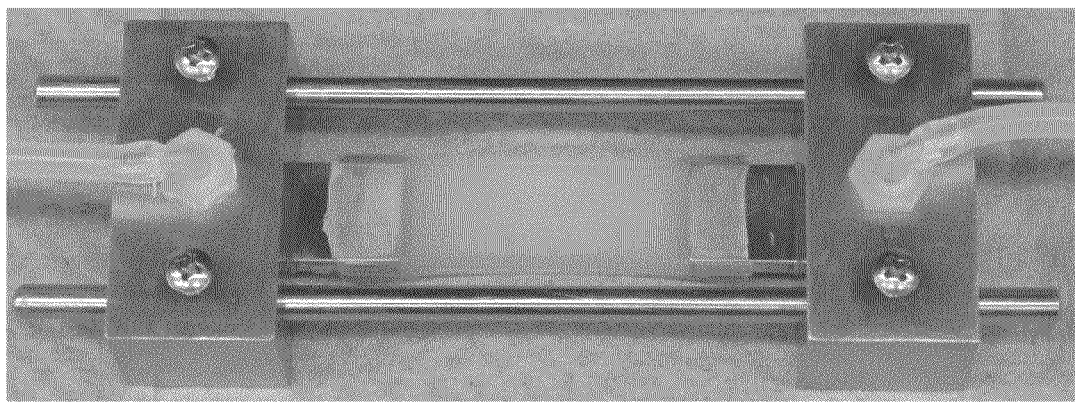
FIG. 16 is a digital image of an embodiment of a bioreactor of the present disclosure designed for a rectangular embodiment of a tissue construct of the present disclosure.

Configurations of 3D Vascularized Scaffolding and Tissue Constructs:

In embodiments, the physical properties (e.g., size, shape, density, etc.) of the 3D vascularized tissue construct and/or the 3D biocompatible vascularized scaffolding can be configured and/or adapted for various applications. For instance, the 3D scaffolds/tissue constructs of the present disclosure can be adapted to have different sizes, shapes, thickness, density, and the like for various assay, culture, imaging, and screening applications, as well as other uses and applications. For instance, in some embodiments, the tissue construct is configured to be placed in a well-plate and/or a flattened parallel plate flow chamber. In other embodiments the tissue construct is configured for placement on a confocal imaging device, a fluorescence imaging device, a phase contrast imaging device, or interchangeably on any of these devices. In embodiments, the tissue construct and/or scaffold of the present disclosure is adapted to be placed in a bioreactor tissue chamber as well as one or more of the other above described devices. For instance, a tissue construct adapted for a well plate format may not need as much structural integrity, so a softer gel matrix scaffolding material may be appropriate. In some embodiments where more structural integrity is desired, a solid porous material, such as RVC, may be included in the scaffolding material. Shape can also be tailored to the appropriate application. For instance, in embodiments for a well plate, a more disk-like structure for the construct may be desired (e.g., FIG. 15A), whereas for use on a confocal imaging device, a more rectangular shape may be appropriate (e.g., FIG. 15B). Also, the shape of the construct may be adapted for use in various bioreactors. For instance, the construct may have a somewhat cylindrical or disk shape (e.g., FIG. 15A) for use in a cylindrical bioreactor, such as shown in FIGS. 4A and 4B, while the construct may have a more rectangular shape (e.g., FIG. 15B) for use in a rectangular bioreactor, such as shown in FIG. 16.

As mentioned above, the present disclosure encompasses not only the three dimensional (3D) vascularized tissue constructs of the present disclosure, but also 3D vascularized biocompatible scaffolds for supporting in vitro, 3D tissue culture. The 3D vascularized biocompatible scaffolds are similar to the tissue constructs, but do not yet include a 3D network of cells within the scaffold material. Thus, these scaffolds can be used, as described above, to grow 3D networks of cells and to make tissue models and disease models as described above. In embodiments, the 3D, biocompatible scaffold material of the present disclosure can include a solid, porous material, a gel matrix material, or a combination thereof, as described above.

The microchannels of vascularized biocompatible scaffolds may or may not include the layer of endothelial cells within the lumen. Endothelial cells could be added to the scaffolds at a later time, before or contemporaneously with the addition of the cells of interest. The present disclosure also includes kits including a 3D biocompatible scaffold of the present disclosure, including the biocompatible scaffolding material and a plurality of microchannels as described above, with or without the endothelial cells lining the lumen of the microchannels. In embodiments, the kit can also include a culture of endothelial cells and/or a culture of other tissue cells of interest, and instructions for adding the endothelial cells and/or other tissue cells of interest to produce a 3D vascularized tissue construct of the present disclosure.

Methods of Making the Tissue Constructs and Scaffolds

The present disclosure also provides methods of making the 3D vascularized tissue constructs and biocompatible scaffolds of the present disclosure and methods of growing a three-dimensional (3D) tissue construct in vitro. In embodiments, methods of making a 3D vascularized scaffold of the present disclosure includes providing a three dimensional (3D) vascularized biocompatible scaffold, where the scaffold includes a 3D, biocompatible scaffold material and a plurality of channels extending through the scaffold, where the channels form lumen for allowing passage of liquid through the scaffold.

In embodiments the method of making the biocompatible scaffold and tissue construct of the present disclosure includes forming the microchannels by using a microchannel construct of the present disclosure, as described above. In some embodiments the microchannels are formed by using the construct to punch channels in the scaffolding material, while in other embodiments, the microchannel construct is inserted into a material for forming the scaffolding material (such as a gel matrix material or a combination of a gel matrix material and solid porous material, and the gel matrix material is cured or gelled around the microchannel construct. Then the construct is removed, leaving channels within the scaffolding material. In embodiments, the method further includes seeding the lumen with endothelial cells, such that endothelial cells line at least a portion of the lumen. Embodiments of making a 3D vascularized tissue construct of the present disclosure further include seeding the scaffold with cells of at least one tissue type. The scaffold can then be perfused with cell culture media including cells of interest (or otherwise contacted with the cells of interest) to seed the scaffold material with the cells of interest. In embodiments, the seeded scaffold material is incubated and a 3D network of cells of the at least one tissue type grows within the scaffold.

Bioreactors

Figure 2:
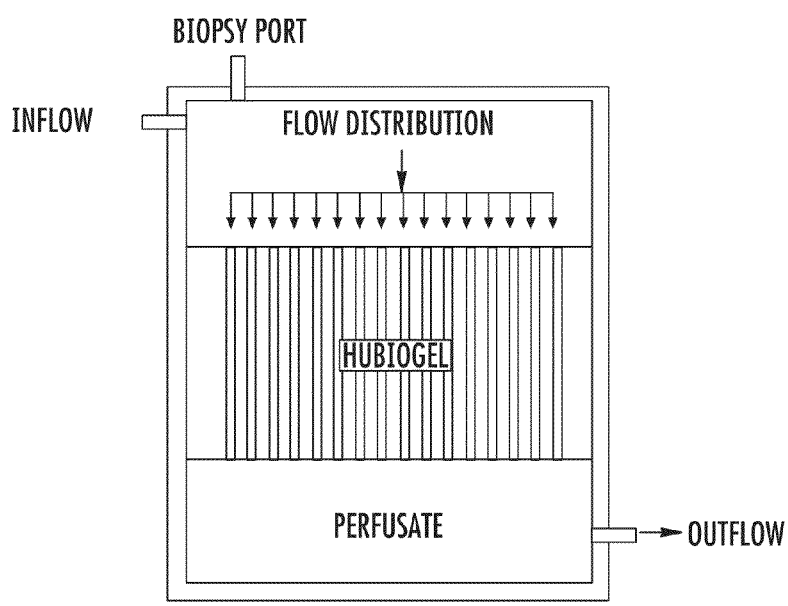
FIG. 2 is a schematic illustration of an embodiment of a bioreactor of the present disclosure including an embodiment of a 3D vascularized tissue construct of the disclosure with HuBiogel forming at least part of the biocompatible scaffold material. Flow rates can be introduced to expose endothelial cells in the channels to fluid shear stress similar to a physiological environment. Perfusate can be collected downstream and tissue biopsying is possible through a biopsy port.

The 3D vascularized tissue constructs of the present disclosure are also adapted to be included in a bioreactor. Bioreactors for housing the tissue constructs of the present disclosure are also included in the scope of the present disclosure. In embodiments, a bioreactor is provided that has a tissue chamber for housing the tissue construct, and upstream and downstream portals for the transfer of fluids (e.g., culture medium) and an optional pump for controlling the flow of culture fluids. A schematic of an embodiment of a bioreactor of the present disclosure is illustrated in FIG. 2. The bioreactors of the present disclosure can be designed and/or adapted for various embodiments of tissue constructs. For example, bioreactors can be adapted for a disk shaped tissue construct, and in other embodiments, the bioreactor can be adapted for a substantially rectangular shaped tissue construct. In embodiments the bioreactors are also compatible with an imaging device, such as a confocal imaging device, a fluorescence imaging device, a phase contrast imaging device, or interchangeably with any of these devices. In embodiments, the bioreactor is configured to allow imaging of the tissue construct while the tissue construct is within the bioreactor.

Figures 3A, 3B:
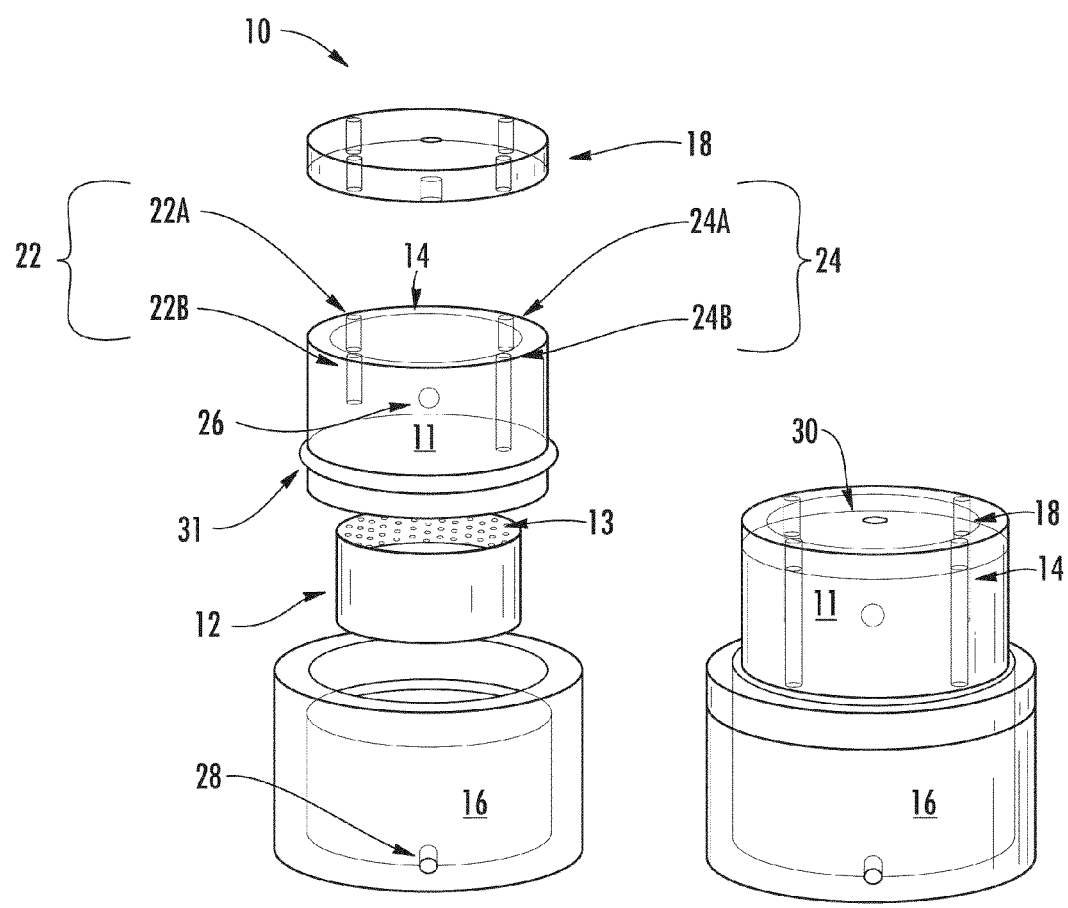
FIGS. 3A-3B illustrate an embodiment of a single bioreactor of the present disclosure including a 3D vascularized tissue construct of the present disclosure. In the embodiment illustrated, the 3D construct has an array of microchannels for enhanced perfusion of the cell-seeded construct.

An embodiment of a representative bioreactor of the present disclosure is shown in FIG. 3, which will be described in greater detail here as a representative embodiment. The bioreactor (10) includes a tissue chamber (11) for housing a 3D vascularized tissue construct (12) having a plurality of microchannels (13). The bioreactor also includes an input area/chamber (14), and output area/chamber (16) and a cap (18). The input and output chambers include portals (20). The input chamber is upstream of the tissue chamber and includes input portals (22) (such as, but not limited to, an input portal (22A) for introducing fresh media bolus and input portal (22B) for introducing fresh assay reagents). Not all embodiments will include every portal illustrated and described here, in that in some embodiments, some input portals may serve to input various items, while some output portals may also be used for a variety of different outputs. In an embodiment, the bioreactor includes upstream output portals (24). In embodiments an output portal (24A) provides a portal for extracting fluid from the construct for analysis. Another output portal, (24B) can provide access to flush fluid, make a media change and the like. In embodiments, the bioreactor also includes a downstream output portal (28) for the exit of perfusate from the output chamber (16). The bioreactor of the present disclosure may also include an input (26) for continuous media flow into the input chamber. In embodiments, the bioreactor also includes a biopsy port (30) for extracting a biopsy sample from the tissue construct and an optional o-ring (31) for a seal to other devices or systems, such as another bioreactor. In embodiments of the present disclosure the tissue construct acts as a barrier between the input and output chambers (14 and 16), such that flow of media introduced by a pump, syringe, etc., flows through the microchannels of the construct.

In embodiments of the bioreactor of the present disclosure, the bioreactor includes a three dimensional (3D), engineered tissue construct comprising a three-dimensional, biocompatible scaffold material (as described above); a three-dimensional network of living cells within the scaffold material; and a plurality of channels extending through the construct, such that a substantial portion of the channels have an inlet at one surface of the construct and an outlet at an opposing surface of the construct, and a plurality of endothelial cells at least partially lining the lumen; a tissue chamber configured to house the tissue construct such that the tissue construct forms a barrier between upstream and downstream flow of media through the chamber directing flow of media through the channels of the tissue construct, where the chamber has at least one input portal upstream of the location of the tissue construct and at least one output portal downstream of the location of the tissue construct; and at least one micropump, syringe pump, or peristaltic pump to control flow of media through the tissue chamber.

Bioreactor Networks/Arrays

As discussed above, the bioreactors of the present disclosure can be adapted to be interconnected to create an array of bioreactors. In the array, different bioreactors can support tissue constructs of different tissue types, such that different tissue types can be interconnected in the array. This allows testing, assaying, observing, analyzing of cellular and other interactions between tissue types. It also allows one to monitor how a proposed therapeutic or other compound exerts an effect on one tissue type and may exert a different effect on another tissue type. This "plug-and-play" design allows one to mix up tissue types and to interconnect tissue types in a configuration more accurately modeling a host system.

In embodiments, a bioreactor network includes an array of interconnected bioreactors according to the present disclosure and at least one pump to control flow of media through the bioreactors, such that the bioreactors in the array are in fluid communication with each other Methods of Screening The present disclosure also includes methods of screening a test compound using the 3D vascularized tissue constructs of the present disclosure. In embodiments, the tissue constructs can be used as a model of diseased and/or healthy tissue to determine the effect of a candidate drug, therapeutic, biological agent, or other compound on the tissues. In embodiments, the method of screening includes providing a three dimensional (3D), engineered, vascularized tissue construct as described above with a network of living cells of a tissue of interest within the scaffold material, exposing the 3D tissue construct to the test compound; and monitoring any changes in the tissue construct after exposure to the test compound, wherein the changes are selected from the group consisting of histological, biochemical, and physiological changes, or a combination thereof. The constructs can be used to monitor no only the responses of a diseased tissue type to a potential drug candidate but also the responses of healthy tissues to the same compound in order to test for toxicity and/or adverse effects.

In embodiments, the tissue constructs of the present disclosure can be used to screen potential breast cancer therapeutic compounds. The compounds can be screened using a tissue construct mimicking human breast cancer diseases (e.g., including breast cancer cells and/or a combination of breast cancer cells, and other healthy, human breast cells.) In such embodiments, the construct, including the 3D breast cancer tissue and/or other diseased or healthy cells is contacted with a test compound (e.g., a potential breast cancer therapeutic). The method includes detecting changes in growth or viability of the breast cancer cell network and/or healthy breast cells after exposure to the test compound. In embodiments, a decrease in growth or viability of the breast cancer cells indicates the test compound is a potential breast cancer therapeutic compound. The method may also include detecting toxicity of the breast cancer therapeutic compound as measured by histological, biochemical, physiological changes, or a combination thereof, of the cell network. These methods and variations of these methods can be used to screen a variety of compounds for effects on various tissue types that can be grown in the 3D vascularized tissue constructs of the present disclosure.

EXAMPLES

Now having described the embodiments of the present disclosure, in general, the examples describe some additional embodiments of the present disclosure. While embodiments of present disclosure are described in connection with the examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

3D Vascularized Tissue Constructs with Gel Matrix Scaffolds

The present Example describes the creation of 3D engineered tissue models for evaluation of breast cancer drug therapies. It is expected that this platform will dramatically reduce the time and cost associated with regulatory approval of an anti-cancer therapies, currently a multi-billion dollar endeavor. Cell/biomaterial models formed in 3D represent an emerging paradigm in drug development in which novel therapeutic compounds are rapidly developed, repurposed or terminated. However, 3D models with a prefabricated vascular network system, which will supply the cells with oxygen and nutrients to larger volumes, have not been previously explored. The prevascularized 3D engineered tissue construct of the present disclosure mimics human breast cancer, providing a 3D model of the disease that will respond to anti-cancer therapeutic intervention in a manner representative of the in vivo human response.

Materials and Methods:

The two scaffolds used were bacterial cellulose and fibrin. Channels were created in each biomaterial through use of a micro channel construct (FIG. 1). The scaffolding materials were prevascularized by forming micro-channels of 250 μm or less in diameter, with the use of a microchannel construct having an array of wires/micro-rods of approximately 250 microns in diameter. For bacterial cellulose constructs, the microchannel construct was inserted into the scaffolding material, a gel matrix material including bacterial cellulose. After insertion of the micro channel construct, the bacterial cellulose matrix material was cured (e.g., "gelled").

After gelation of the matrix material to form the scaffolding, the microchannel construct was removed, leaving an array of microchannels through the scaffolding construct. For fibrin gel constructs, the microchannel construct was punched into the gel matrix material of fibrin gel after gelation; removal of the microchannel construct left an array of microchannels through the fibrin gel scaffolding construct.

Figure 5:
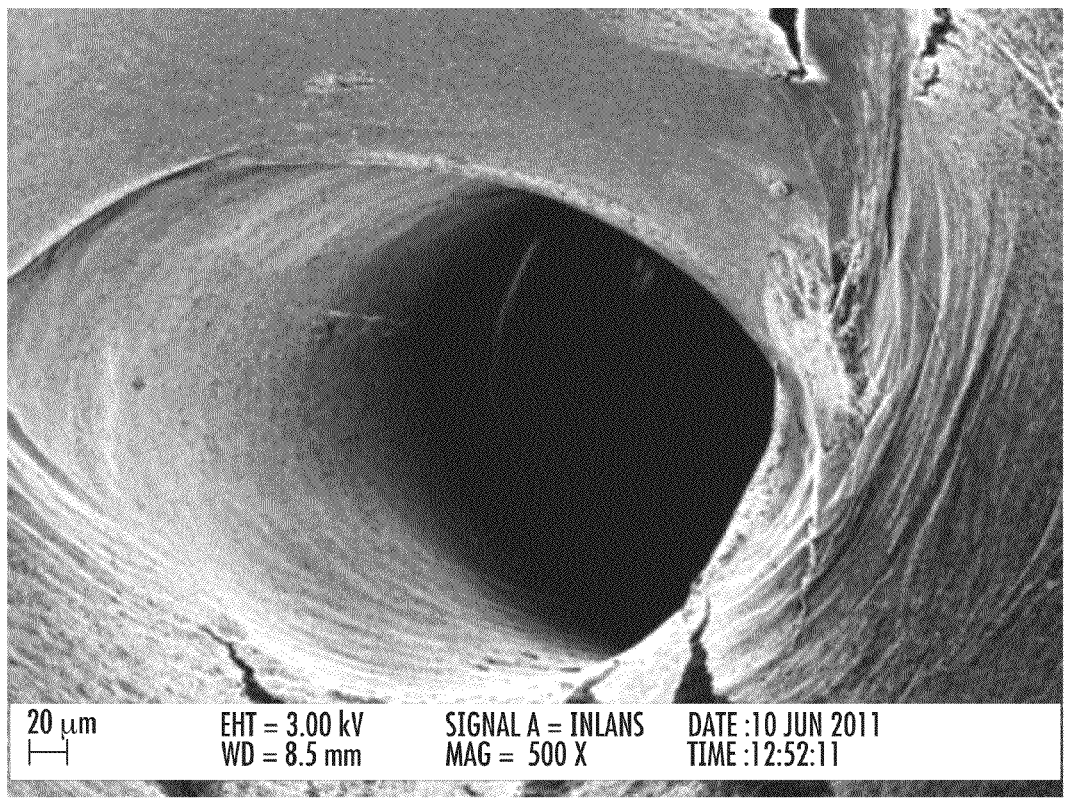
FIG. 5 illustrates a digital image of embodiments of microchannels in 3D tissue constructs of the present disclosure at 500× magnification.

SEM was used to image the channels (FIG. 5). The bacterial cellulose channels were then endothelialized by perfusion of HUVECs through a bioreactor system.

Results:

SEM confirmed that micro channels were formed after introducing the micro channel construct. FIG. 5 shows an SEM image of a microchannel in bacterial cellulose gel scaffolding material. Histology and H&E staining verified the channels were lined with a confluent layer of endothelial cells. Imaging also confirmed endothelial cells lining the lumen of microchannels in a construct made with bacterial cellulose scaffolding material (not shown).

Conclusion:

Bacterial cellulose and fibrin have both been shown to support channel fabrication through SEM images. In addition, H&E staining has shown that the bacterial cellulose channels were endothelialized to create a prevascularized scaffold to support growth of other cellular networks such as fibroblasts and breast cancer cells. Therefore, both bacterial cellulose and fibrin represent promising scaffolding materials for construction of the prevascularized, 3D co-culture model biomaterial for mimicking human breast cancer environments.

Example 2

Bioreactor with 3D Vascularized Tissue Constructs with Gel Matrix Scaffolds Example 1 above describes successful creation of prevascularized 3D volumes within hydrogel biomaterials; the present example describes growth of mammalian cells on scaffolds of the present disclosure and construction of bioreactors for the growth, maintenance, and observation/analysis of the tissue constructs.

The tissue constructs of the present example included human breast cancer cells. Two biomaterials were selected for the creation of the prevascularized scaffolds to support breast cancer cells: bacterial cellulose and fibrin gel. As described in example 1, above, these materials were successfully prevascularized with microchannels less than about 250 μm in diameter, and these microchannels were seeded with vascular endothelial cells demonstrating that the microchannels can support a confluent vascular endothelial layer. The present example demonstrates further seeding the 3D prevascularized tissue constructs with breast cancer cells and that these tissue constructs of the present disclosure can be continuously perfused in a flow bioreactor. This example demonstrates that such constructs and bioreactors can serve as the basis for development of a viable 3D co-culture that supports breast cancer epithelial cells, breast fibroblasts, and vascular endothelial cells.

Bioreactor Design

FIG. 2 is a schematic drawing of the tissue construct chamber of a bioreactor of the present disclosure, as used in the present example, including a 3D vascularized tissue construct within the chamber. A cylindrical flow-through bioreactor as illustrated in the schematic of FIG. 3 and as shown in the image of FIGS. 4A and 4B was constructed of polycarbonate in order to subject the micro-channels to pulsatile flow with culture media. The bioreactor was designed so that the prevascularized disc-shaped biomaterial could be mounted into a larger disc-shaped seat and placed inside the cylindrical flow-through chamber. The biomaterial and the seat represent a partition between the upstream and downstream flow, thus forcing media to pass through the array of micro-channels. Two lids sealed the bioreactor and enabled the upstream silicone tubing to be connected to the pump and the downstream tubing to act as a return to the reservoir. As described in Example 1, above, micro-channels for bacterial cellulose were formed around an array of 250 μm diameter wires, whereas micro-channels for fibrin were formed by punching the array into the scaffold after gelation. A stainless steel sheet with dimensions of 5 mm×5 mm×1 mm was used as the micro-channel construct base. Scanning electron microscopy confirmed that microchannels in bacterial cellulose and fibrin were formed after introducing the micro-channel constructs. H&E staining showed a confluent layer of endothelial cells in the bacterial cellulose channels as well. However, the bacterial cellulose channels were irregular in shape and had uneven and funnel shaped channel openings. A multi-culture of human breast cancer cells (MDA-MB-231) and human breast fibroblasts (HT1080) were seeded into the fibrin scaffolding constructs and successfully grown and maintained in culture for 2 weeks.

3D Microphysiologic Bioreactor

Media flow through each prevascularized tissue construct bioreactor system is provided by commercially available high performance micropumps. These micropumps are suited to deliver precise flow of media to each tissue chamber. The micropump will perfuse the tissues with media specific to the tissue type. The total flow through each 3D tissue is uniformly distributed through each cylindrical channel within the tissue. Flows are governed by the Navier-Stokes equations, which can be simplified in microfluidic systems as the ratio of the inertia terms to the viscous terms (characterized by the Reynolds number Re) becomes negligible (Re<<1). This results in applying the Stokes equation to estimate microchannel pressure gradients:

$$0 = -\nabla p + \mu \nabla^2 \vec{u}$$

where p is pressure, u is fluid velocity, and μ is the dynamic viscosity of the media. In the case of cylindrical microchannels, a parabolic flow develops and the relation for shear stress can be described by the Hagen-Poiseuille equation:

$$\tau = \frac{4\mu Q}{\pi r^3}$$

Where τ is the fluid of media in the channel shear stress at the channel wall, Q is the volumetric flow rate, r is the radius of the channel and μ is the dynamic viscosity of the media. For the purpose of estimating shear stress at the walls of the microchannels, the media will be assumed to be single-phase Newtonian, rigid wall boundary with no slip at the wall.

Microchannels are cast within the tissue construct as described above and the tissue is perfused with media using the micropump. For a HuBiogel construct of 10 mm diameter and 3 mm thick, with a 20×20 mm array of 250 micron diameter microchannels (total=400), if each microchannel is 0.250 mm in diameter, then the total cross sectional area is $400(\pi r^2) = 400(\mu \pi \cdot 125^2) = 20$ mm$^2$. The total volume of media contained within the microchannel system is about 60 mm$^3$ or 60 microliters. A mean volumetric flow rate (in the case of pulsatile flow from the peristaltic pump) of 60 microliters per minute yields a wall shear stress of approximately 8-10 dynes/cm$^2$ within each channel.

Example 3

3D Vascularized Tissue Constructs with Porous Solid and Gel Matrix Combination Scaffolds Cell culture using matrices to enhance cell growth is well known (e.g. Matrigel, HuBiogel). 3D cell culture is a rapidly advancing field where, for example, tumor cells can be grown that represent more closely the tumor microenvironment found in an in-vivo setting. This latter fact has led to an increased use of these 3D cell cultures to be used in a variety of drug screening assays. However, one of the problems in using the 3D and/or matrigel approach is that the spheroids formed in this manner can form necrotic cores and can shrink as they grow to a useable size, at least partially due to the lack of access to media including nutrients, oxygen, etc.

The examples above demonstrate the potential of forming 3D vascularized tissue constructs to support growth of cellular networks in a more physiologic environment. The present example demonstrates using a variety of novel materials to act as scaffolds for a variety of cell culture applications. The applications of these materials and this technology could include growth of tumor cell cultures and co-cultures without the need for a gel support or in combination with gel support to enhance structural integrity. The use of such materials also can also support the growth of physiologically relevant microphysiological systems (e.g. miniature organs or disease models (e.g., breast tumor models) to be used in place of animals during drug development) and as a mechanism to create potential synthetic blood vessels in the form of endothelialized microchannels through one or more of these materials.

Figure 6:
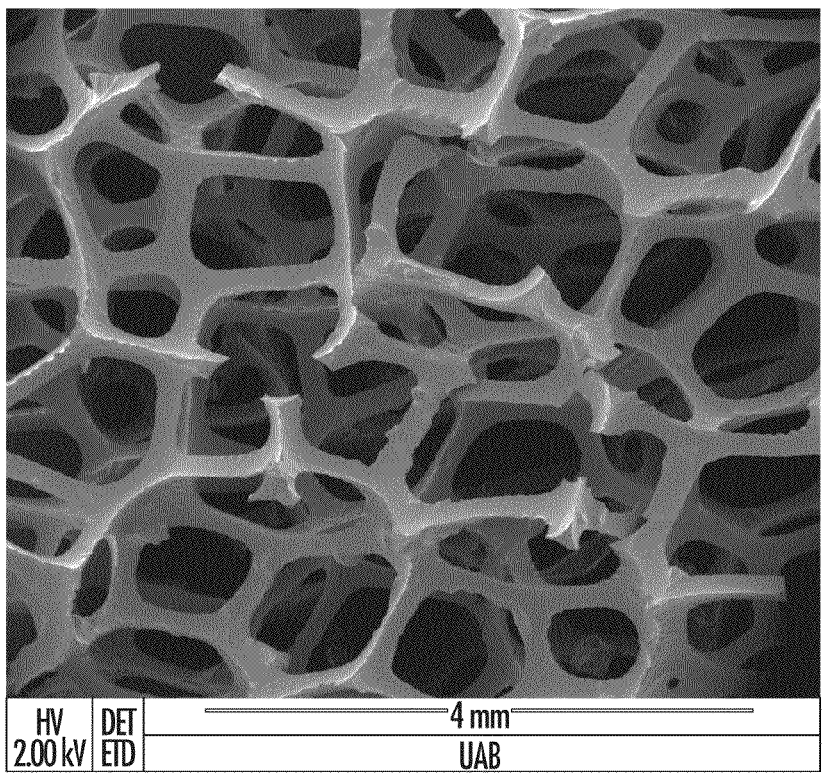
FIG. 6 is an EM image taken at 10× magnification of commercially available reticulate vitreous carbon (RVC) showing the lattice-like structural framework provided by the open pore network. Scale bar is 4 mm.
Figure 13A:
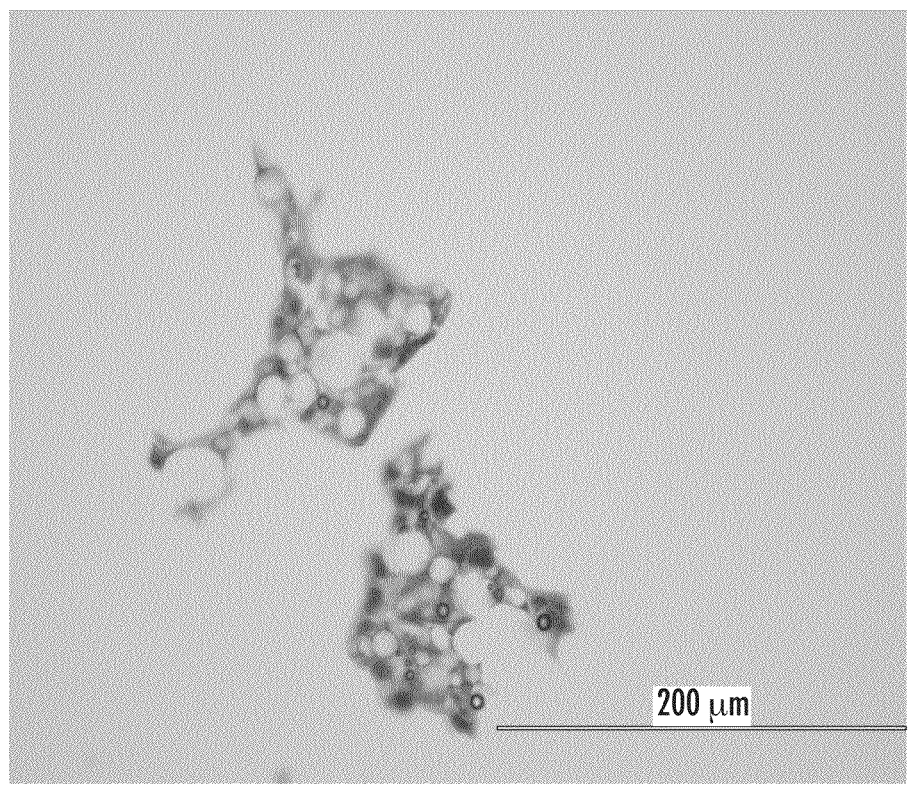
FIGS. 13A-13B are images of MDA-MB-231 cells grown on different scaffolding materials of the present disclosure. Scale bars are 200 microns.
Figure 13B:
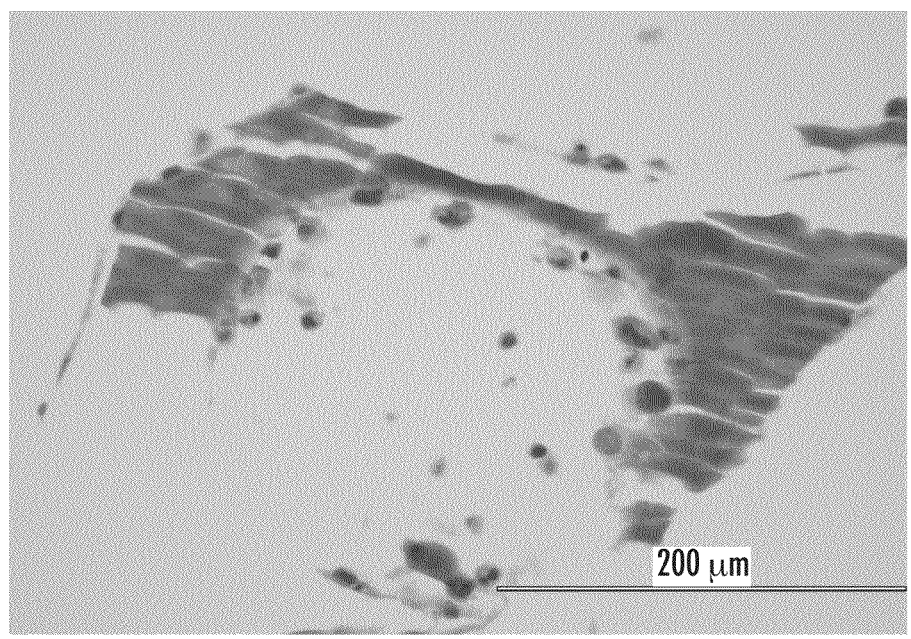

The scaffolding materials used in the present example include a variety of aerogels obtained from Southern Research™ and commercially available materials in the form of a reticulate vitreous carbon (RVC) (FIG. 6) having various pore sizes. RVC, also known as glassy carbon foam and available under the trade name Ultrafoam™ was obtained from Ultramet™, Pacoima, Calif. Aerogels/Solgels are made according to a process where glass beads, aerogel, or nanofibers are coated with amphiphile and foamed in an aqueous solution. Solgel is added as a locking agent to hold the foam in place. The solgel can be thermally removed by heating to 600 degrees C. Alginate or gelatin can also be used as a locking agent. An aerogel used in the present example from Southern Research™ had a specific chemical composition of formaldehyde/resorcinol/amphiphile (gallic acid, ethyl ester) (FIGS. 13A and 13B). Aerogels can be made according to the process described in the following publications (both of which are incorporated herein by reference): Pekala, R. W. et al., "Resorcinol-Formaldehyde Aerogels and Their Carbonized Derivatives." 1989. American Chemical Society Division of Polymer Preprints. 30: 221-223; and Pekala, R. W., et al., "Carbon Aerogels for Electrochemical Applications." 1998. Journal of Non-Crystalline Solids 225: 74-80.

Experimental Conditions

Medium: DMEM with 10% FBS and 1% PSG, Plate: 12 well cell culture cluster plate (Corning #3513), Cell line: breast cancer MDA-MB-231 (RFP stable line), Cell seeding: 250,000 cells/well/2 ml of medium, Incubation: 37° C. and 5% of $CO_2$, Medium change: every 2-3 days, Moved the aerogels into a new plate on day 8.

FIG. 7 represents a particle stabilized foam. Incorporated into the foam were 3M silica microbubbles. Resorcinol-formaldehyde was used as a matrix to strengthen the RVC foam. In this Example, the foam was incubated with breast cancer cells.

Furthermore, these constructs were successfully sectioned these materials in the normal manner for histopathology, and it was possible to employ other standard cellular and molecular assessment protocols of cell and tissue function. Processing the samples using conventional H&E demonstrates that cells have managed to infiltrate the individual pores and remain viable over a period of time.

Figure 8:
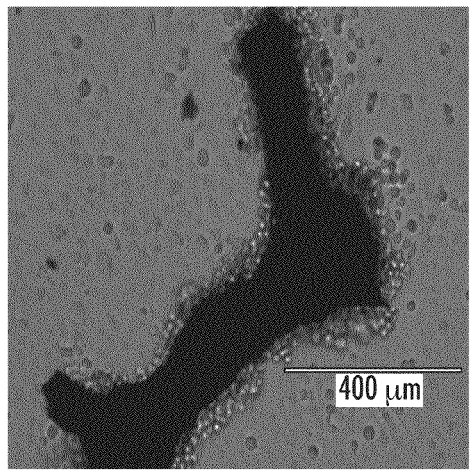
FIG. 8 is a PCM image of MDA-MB-231 cells grown on RVC 45 pores per inch (ppi) at day 7. 3D cell clumps can be seen developing around the material, as compared to (2D) planar cells in the background. Scale bar is 400 microns.
Figure 9:
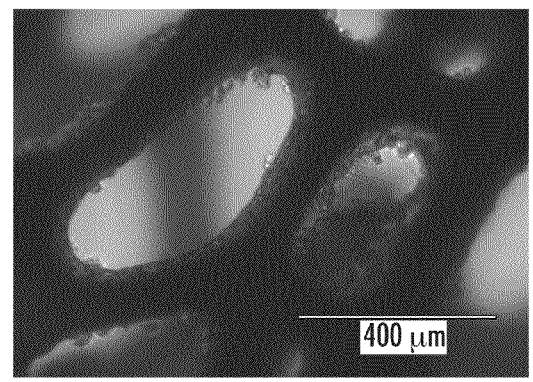
FIG. 9 is a PCM image of MDA-MB-231 tumor cells grown on RVC 45 pores per inch (ppi) at day 11. Cell adhesion is visible on the inside of individual pores of the scaffolding material. Scale bar is 400 microns.
Figure 10:
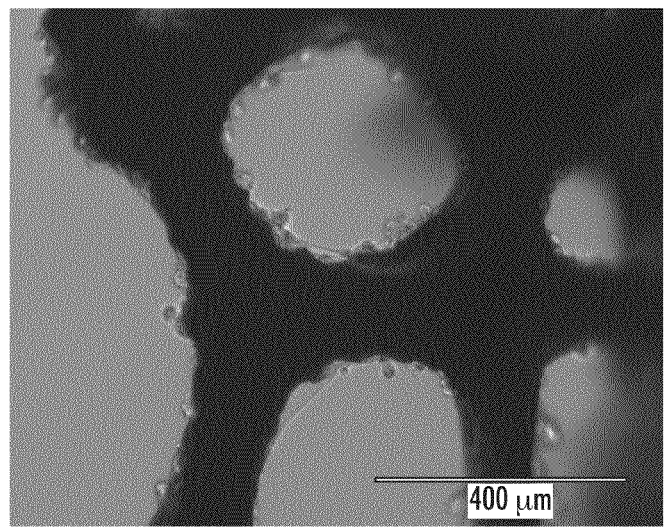
FIG. 10 is an image of MDA-MB-231 tumor cells grown on RVC 45 pores per inch (ppi) at day 16. Scale bar is 400 microns.
Figure 11:
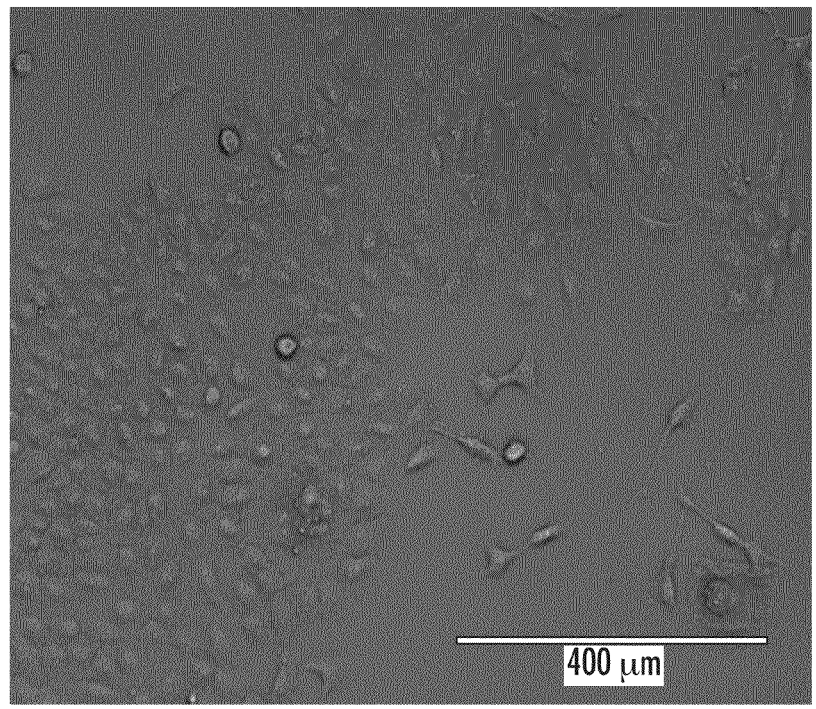
FIG. 11 is an image of a 2D control of MDA-MB-231 tumor cells grown on a planar substrate as opposed to a 3D scaffold material at day 16. Scale bar is 400 microns.
Figure 12:
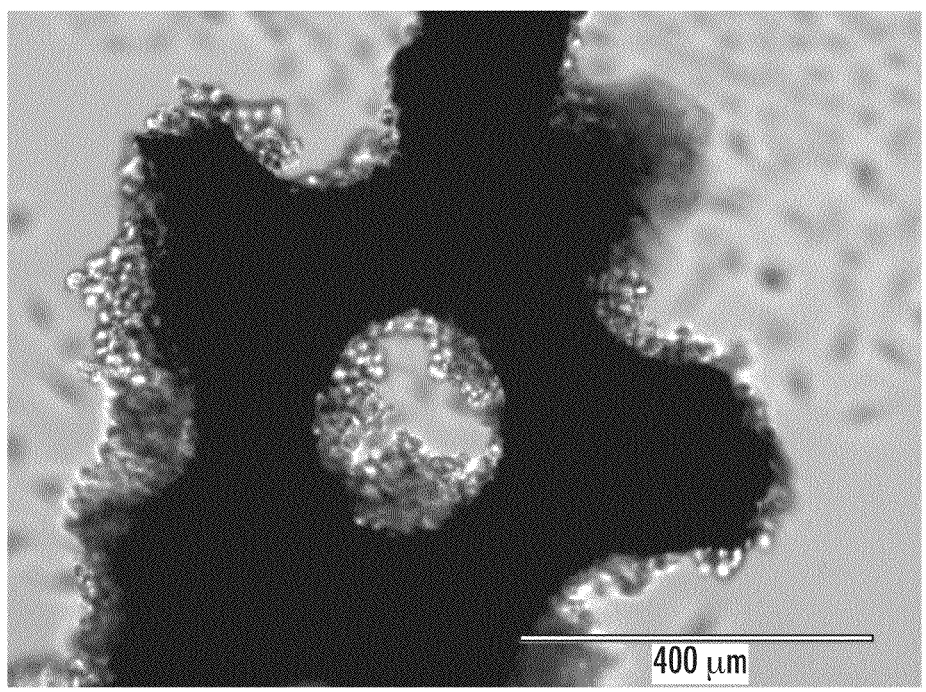
FIG. 12 is an image of MDA-MB-231 tumor cells grown on RVC 65 pores per inch (ppi) at day 17. Scale bar is 400 microns.

All scaffolds prepared in this example supported viability of various cell types in appropriate physiological media, O2/CO2 environment, at 37 degrees. FIGS. 8-10 are images taken of RVC foam supporting growth of MDA-MB-231 breast cancer tumor cells grown on RVC 45 pores per inch (ppi) at different days. FIG. 12 shows MDA-MB-231 cell grown on RVC 65 ppi. FIG. 11 represents a control, showing an image of the MDA-MB-231 cells grown on a flat substrate. FIG. 7 shows MDA-MB-231 cells grown on the particle stabilized foam described above. FIG. 13A shows the MDA-MB-231 cells grown on the aerogel scaffolding material described above.

Example 4

Tissue Constructs and Bioreactor for RVC-Based Scaffold 3D Vascularized Tissue Constructs The present example demonstrates that an extracellular matrix scaffold has been developed to mimic the native extracellular matrix and includes growth of relevant cell types (e.g., human breast cancer epithelial cells and human breast fibroblasts) along with the prefabricated vascular network (prevascularization). These systems are intended to support long-term growth, recapitulate physiological tissue function, and accurately model response to treatment. The use of these 3D vascularized tissue constructs that can support growth of reproducible tissue volumes will transform breast cancer drug development by providing reliable, cost-effective models that can more accurately predict therapeutic efficacy than current preclinical in vivo and in vitro models.

Experimental Methods

Perfusion Bioreactor Design

Two versions of the perfusion bioreactor were been designed and fabricated. The first, a disc shape, is compatible with a 12 well-plate format (FIG. 15A). The second, a rectangular volume, is suitable for confocal imaging (FIG. 15B). Endothelial cell (EC)-rich media was pumped through the micro-channels in a closed-loop system. The peristaltic pump induced unsteady flow. A syringe pump was used for one way flow of short-term experiments. In both configurations, the scaffolds acted as a divider between upstream and downstream flow forcing the media to flow through the fabricated micro-channels in the scaffolds.

Scaffold & Micro-Channel Fabrication

Scaffolds were either composed of reticulated vitreous carbon (RVC) and collagen measuring 10 mm in diameter×3 mm in height or composed of RVC, collagen, and Matrigel measuring 10 mm in width×5 mm in length×2.4 mm in height. Prior to gelation, 400 micron diameter stainless steel rods were soaked in 25% glutaraldehyde, air-dried, and then injected into the RVC foam pores length-wise. For the RVC/collagen scaffolds, a solution of 1.5 mg/ml collagen was injected into the RVC pores. For the RVC/collagen/Matrigel scaffolds, a solution of 1.9 mg/ml collagen containing 10% Matrigel was composed by mixing 14.7% (v/v) of DMEM/10% FBS, 1.9 mg/ml collagen, 10% (v/v) of 10× media, 10% (v/v) of Matrigel and 0.524 M of sodium bicarbonate. The collagen/Matrigel solution was injected into the RVC pores.

For gelation of collagen/matrigel mixed scaffolding, frozen Matrigel and collagen was thawed in ice. Cell culture media and sodium bicarbonate were kept cold on ice as well. The following components were mixed in the stated order in a 2 ml microcentrifuge tube for creation of a 1.9 mg/ml concentration collagen solution containing 10% (v/v) Matrigel: 1) Media or deionized water—137 µl, collagen—633 µl (drop-wise), Matrigel—100 µl, 10× volume of media—100 µl, sodium bicarbonate—30 µl (drop-wise). The tube was gently inverted until color is homogeneous. Using a 1 ml syringe, 0.3 ml of the liquid solution was withdrawn. A 27 Gauge needle was added to the end of the syringe and solution was inserted into RVC samples having microchannel construct in place, being careful not to touch the microchannel construct wires with the liquid. The PDMS tube/RVC/matrix construct was placed in a petri dish and wrapped with parafilm. A vacuum was used to de-gas and remove bubbles by allowing the vacuum to get down to at 4 inHg. Samples were moved to an incubator for 45 minutes to allow for gelation of Matrigel and collagen.

Figure 14A:
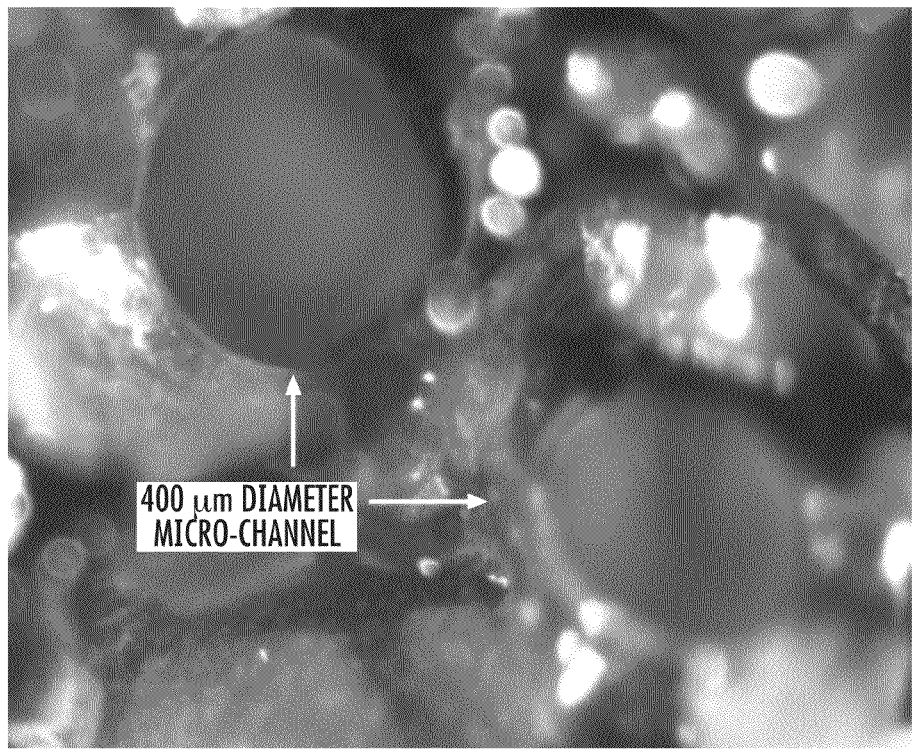
FIGS. 14A-14D are images of embodiments of vascularized scaffolding constructs of the present disclosure.
Figure 14B:
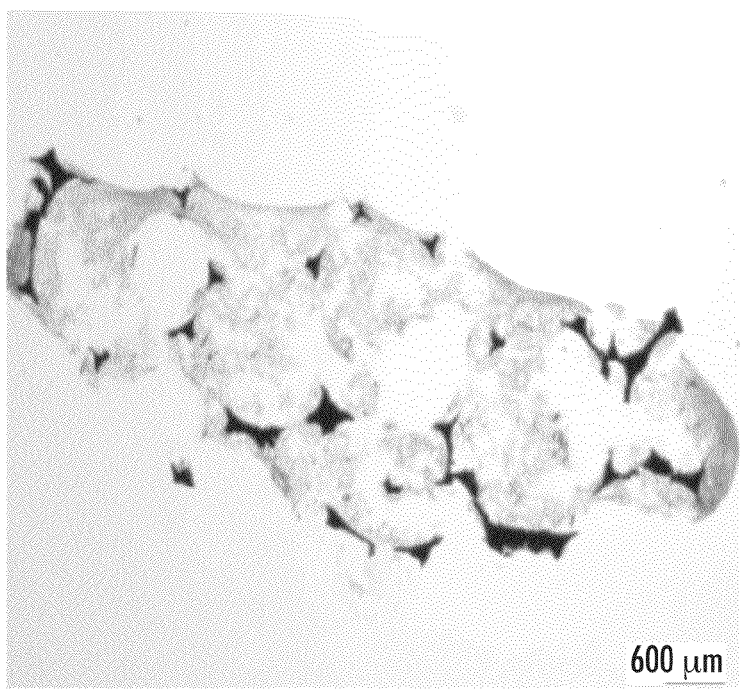

After gelation of all scaffolds, the rods were gently removed to form the micro-channels, which are shown in the images of FIGS. 14A and 14B.

Bioreactor Version 1—Micro-Channel Endothelialization

RVC/collagen scaffolds were placed in the bioreactor. To statically seed the fabricated micro-channels with endothelial cells, $2.44 \times 10^8$ of rat brain endothelial cells (RBEC) were cultured and plated on top of each scaffold. The bioreactor was sealed and placed into the incubator (37° C., 5% $CO_2$) for 30 minutes to statically seed the micro-channels with RBECs. The primed tubing was hooked up to the bioreactor, reservoir, and peristaltic pump, the pump was turned on, and the bioreactor was left in the incubator (37° C., 5% $CO_2$) overnight to dynamically seed the micro-channels with RBECs. Then, the bioreactor was disassembled and the scaffold was formalin-fixed, processed, paraffin wax-embedded, and sectioned with a microtome. The sections were H&E stained. Hematoxylin stained the nuclei purple and eosin stained the cytoplasm pink.

Bioreactor Version 1—Co-Culture Viability

The collagen/RVC scaffold was prepared as before, but the DMEM/10% FBS media contained a cell suspension of $7.5 \times 10^6$ cells/ml human breast cancer epithelial cells (MDA-MB-231) and $2.5 \times 10^6$ cells/ml human breast fibroblasts (F080). In addition, the gels were gelled in a 12-well plated instead of the perfusion bioreactor. After 45 minutes in the incubator to allow for gelation, 1 ml of media was placed on top of the scaffolds. The scaffolds were left in the incubator for 3 days and then they were sectioned and H&E stained.

Bioreactor Version 2—Micro-Channel Endothelialization

RVC/collagen/Matrigel scaffolds were placed in a 48-well plate. To statically seed the fabricated micro-channels with endothelial cells, RBEC-rich media ($16.1 \times 10^6$ cells/scaffold) was added in the 48-well plate housing the scaffolds. These scaffolds were placed in the incubator (37° C., 5% $CO_2$) for 3 days to allow for static seeding of the micro-channels.

Results & Discussion

H&E staining confirmed that the micro-channels in RVC/collagen and RVC/collagen/Matrigel were formed after introducing the stainless steels rods prior to gelation and that the collagen and collagen/Matrigel both infiltrated into the RVC foam pores. Additionally, H&E staining showed a monolayer of endothelial cells lining the RVC/collagen micro-channels. Finally, H&E has shown survival of a co-culture of cells (e.g., MDA-MB-231 and F080s) in the collagen scaffolds.

Figure 14C:
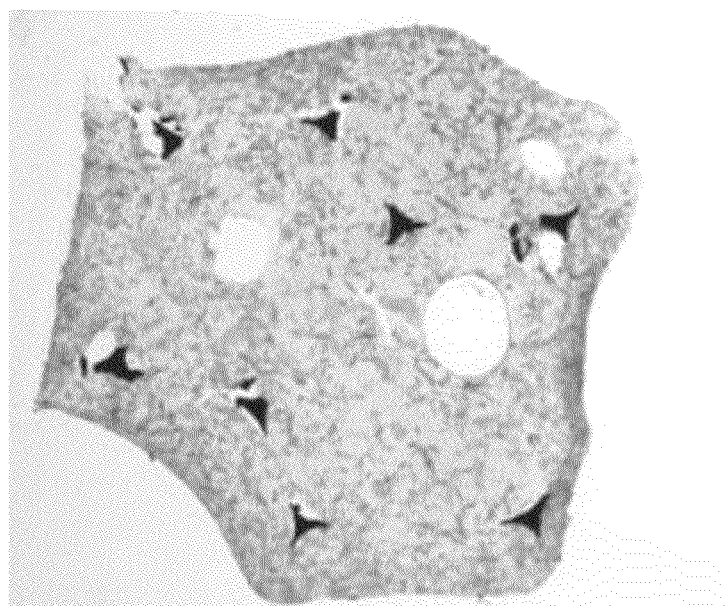
Figure 14D:
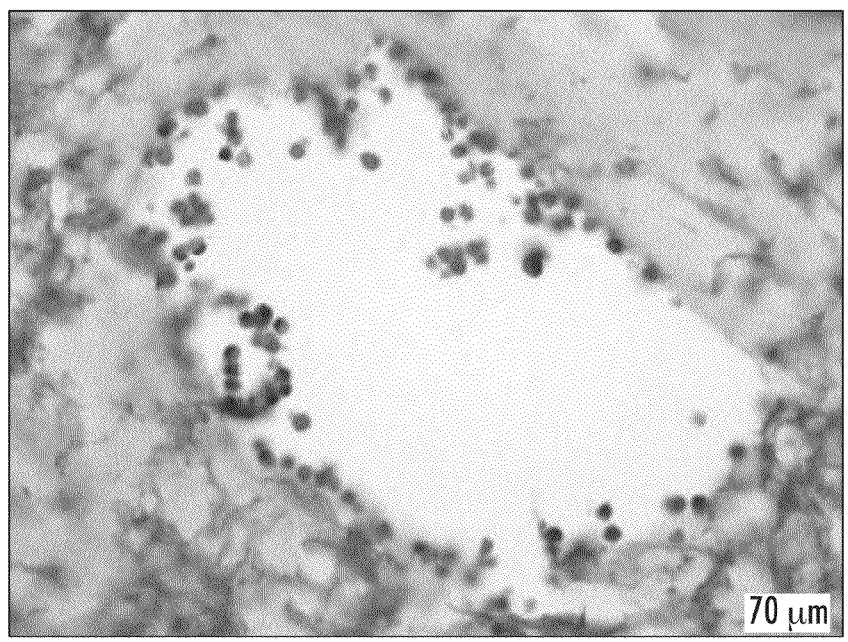

FIGS. 14A-14D show images of vascularized scaffolding constructs of the present example. A 45 ppi collagen/RVC scaffold (1.5 mg/ml collagen/RVC) with two 400 micron diameter micro-channels shown penetrating through the 4 mm thick RVC/collagen scaffold is shown in FIG. 14A. FIG. 14B shows an image of a collagen/Matrigel/RVC scaffold (1.9 mg/ml collagen/Matrigel/RVC, 45 ppi) with three 400 micron diameter micro-channels through the scaffold. FIG. 14C is an image of a section through a collagen/RVC/Matrigel scaffold material with the microchannels visible as the open circular shaped areas, and portions of the RVC scaffolding material visible as the black portions. FIG. 14D is an image of a section (20 um) through gel material showing a cross-section of a single microchannel with endothelial cells lining the interior surface of the microchannel.

These results demonstrate the successful endothelialization of fabricated micro-channels in a 3D volume under conditions of flow. Fluid volumetric flow rates through these 3D constructs and fluid shear stress, in particular cyclic shear stress, at the walls of these channels have not yet been calculated. Since exposure of the endothelium, a monolayer of endothelial cells lining blood vessel walls, to oscillating fluid shear stresses and circumferential cyclic strain from the pulsatile blood flow maintains the physiological state of the blood vessels, mimicking or approximating these stresses in the bioreactor help to create physiological biomaterial/cell scaffolds [5]. In addition, endothelial transport of oxygen, nutrients, waste, and candidate therapeutics is dependent in part on the fluid shear stress that is imparted at the endothelium. Thus, these micro-channels not only provide a conduit for fluid media, cell culture, growth factors, and the like, but it is also hoped that they can develop additional capillary functions such as extracting oxygen from fluid media.

Conclusions

Prevascularized engineered tissues have the potential to revolutionize tissue replacement for diseased or traumatized tissues [6]. In addition to tissue replacement, the prevascularized 3D constructs also have the potential to mimic multiple disease states for drug development.

This example demonstrates successful creation of 3D volumes of RVC/collagen and RVC/collagen/Matrigel exceeding the diffusion distance of oxygen by prevascularizing these scaffolds. In the case of collagen, micro-channels were created and successfully endothelialized within the constructs, and a co-culture of cells was grown within the vascularized constructs. These results set the stage for highly-defined 3D tissue volumes that are perfused and can be used for the evaluation of anti-cancer therapies using primary human cell lines or cells extracted from breast cancer patients. Future work will include complete endothelialization of RVC/collagen/Matrigel scaffold micro-channels, growth of MDA-MB-231s and F080s in RVC/collagen/Matrigel scaffolds, and quantification of fluid mechanical parameters of micro-channel wall shear stress.

In regard to the discussion herein including the Examples above and the claims, it should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include $\pm1\%$, $\pm2\%$, $\pm3\%$, $\pm4\%$, $\pm5\%$, $\pm6\%$, $\pm7\%$, $\pm8\%$, $\pm9\%$, or $\pm10\%$, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and protected by the following claims.

REFERENCES

All of the references are incorporated herein in pertinent part.
1. Birgersdotter A, Sandberg R, Ernberg I: Gene expression perturbation in vitro—a growing case for three-dimensional (3D) culture systems, Semin Cancer Biol 2005, 15:405-412
2. "FDA Issues Advice to Make Earliest Stages of Clinical Drug Development More Efficient." FDA. January 2006. <http://www.fda.gov/NewsEvents/Newsroom/PressAnnouncements/2006/ucm108576.ht m>
3. "U.S. Breast Cancer Statistics." BreastCancer.org. October 2012. <http://www.breastcancer.org/symptoms/understand_bc/statistics>.
4. Kim S S, Utsunomiya H, Koski J A, Wu B M, Cima M J, Sohn J, Mukai K, Griffith L G, Vacanti J P: Survival and function of hepatocytes on a novel three-dimensional synthetic biodegradable polymer scaffold with an intrinsic network of channels, Ann Surg 1998, 228:8-13
5. Davies, P. F. 1995. "Flow Mediated Endothelial Mechanotransduction." Physiological Reviews. 75: pp. 519-51.
6. Wu, X. et al. 2004. "Tissue Engineered Microvessels on 3D Biodegradable Scaffolds Using Human Endothelial Progenitor Cells." Am J Physiol Heart Circ Physiol. 287: pp. H480-7.
7. Pec, Martina et al. 2010. "Reticulated Vitreous Carbon: A Useful Material For Cell Adhesion and Tissue Invasion." European Cells and Materials. 20: 282-94.
8. Pekala, R. W. et al., "Resorcinol-Formaldehyde Aerogels and Their Carbonized Derivatives." 1989. American Chemical Society Division of Polymer Preprints. 30: 221-223.

9. Pekala, R. W., et al., "Carbon Aerogels for Electrochemical Applications." 1998. Journal of Non-Crystalline Solids 225: 74-80.

The invention claimed is:

1. A method of screening a test compound comprising:
providing a three-dimensional (3D), engineered, vascularized tissue construct comprising:
  a 3D, biocompatible scaffold material comprising a solid, porous material and a gel matrix material, wherein the solid, porous material is chosen from the group consisting of: aerogels, reticulate vitreous carbon, and particle stabilized foam, and wherein the gel matrix material is chosen from the group consisting of: synthetic hydrogels, naturally-derived hydrogels, and a combination thereof;
  a 3D network of living cells of a tissue of interest within the scaffold material;
  a plurality of microchannels extending through the construct, such that a substantial portion of the channels have an inlet at one surface of the construct and an outlet at an opposing surface of the construct, wherein the channels form lumen for allowing passage of liquid through the construct; and
  a plurality of endothelial cells at least partially lining the lumen, wherein the endothelial cells result from cells seeded within the lumen of the microchannel and the 3D network of living cells in the scaffold material results from cells seeded within the scaffold material, outside the microchannels;
exposing the 3D tissue construct to the test compound; and
monitoring changes in the tissue construct after exposure to the test compound, wherein the changes are selected from the group consisting of histological, biochemical, and physiological changes, and a combination thereof.

2. The method of claim 1, wherein the biocompatible scaffold material comprises a gel matrix material and further comprises a crosslinking agent, a gelling agent, or a combination thereof that increases the structural stability of the gel matrix material.

3. The method of claim 1, wherein the synthetic hydrogel is selected from the group consisting of: alginate, biocompatible polymer hydrogels, biocompatible copolymer hydrogels, polyethylene glycol (PEG) based hydrogels, and combinations thereof.

4. The method of claim 1, wherein the naturally-derived hydrogel is selected from the group consisting of: collagen, fibrin, elastin, keratin, bacterial cellulose, animal-derived basement membrane extract, and combinations thereof.

5. The method of claim 1, wherein the biocompatible scaffold material comprises reticulate vitreous carbon and a gel matrix material selected from the group consisting of: bacterial cellulose, collagen, fibrin, elastin, keratin, animal-derived basement membrane extract, and combinations thereof.

6. The method of claim 5, wherein the biocompatible scaffold material comprises a combination of reticulate vitreous carbon, collagen and a second gel matrix material selected from animal-derived basement membrane extract.

7. The method of claim 1, wherein the tissue construct is configured to be placed in a well-plate or a flattened parallel plate flow chamber.

8. The method of claim 1, wherein the tissue construct is configured for placement on a confocal imaging device, a fluorescence imaging device, a phase contrast imaging device, or interchangeably on any of these devices.

9. The method of claim 1, wherein the microchannels have a diameter of about 200 to about 450 microns.

10. The method of claim 1, wherein the microchannels have a diameter of about 250 microns or less.

11. The method of claim 1, wherein the 3D network of living cells and the plurality of endothelial cells within the lumen of the microchannel comprise mammalian cells, wherein the 3D network of living cells are pathologic or healthy mammalian cells or a combination thereof.

12. The method of claim 1, wherein at least a portion of the cells within the 3D network of living cells comprises diseased cells and wherein the test compound comprises a drug candidate for treating the disease.

13. The method of claim 1, further comprising placing the tissue construct in a tissue chamber configured to house the tissue construct such that the tissue construct forms a barrier between upstream and downstream flow of media through the chamber directing flow of media through the channels of the tissue construct, wherein the chamber has at least one input portal upstream of the location of the tissue construct and at least one output portal downstream of the location of the tissue construct, wherein the tissue chamber is coupled to at least one pump to control flow of media through the tissue chamber.

14. A method of screening a potential cancer therapeutic compound comprising:
providing a three-dimensional (3D), engineered, vascularized cancer tissue construct comprising:
  a 3D, biocompatible scaffold material comprising a solid, porous material and a gel matrix material, wherein the solid, porous material is chosen from the group consisting of: aerogels, reticulate vitreous carbon, and particle stabilized foam, and wherein the gel matrix material is chosen from the group consisting of: synthetic hydrogels, naturally-derived hydrogels, and a combination thereof;
  a 3D network of living cells within the scaffold material comprising cancer cells or a combination of cancer cells and non-cancerous cells;
  a plurality of microchannels extending through the construct, such that a substantial portion of the channels have an inlet at one surface of the construct and an outlet at an opposing surface of the construct, wherein the channels form lumen for allowing passage of liquid through the construct; and
  a plurality of endothelial cells at least partially lining the lumen, wherein the endothelial cells result from cells seeded within the lumen of the microchannel and the network of living cells results from cells seeded within the scaffold material, outside the microchannels;
exposing the 3D cancer tissue construct to a test compound; and
detecting changes in growth or viability of the cancer cell network after exposure to the test compound, wherein a decrease in growth or viability of the cancer cells indicates the test compound is a potential breast cancer therapeutic compound.

15. The method of claim 14, wherein the non-cancerous cells comprise fibroblasts, epithelial cells, human tissue cells, or a combination thereof.

16. The method of claim 14, wherein the 3D network of living cells comprise breast cancer cells, and the 3D network of cells forms a breast cancer tumor.

17. The method of claim 14, wherein the 3D network of living cells comprise breast cancer cells and non-cancerous breast tissue cells, and wherein the 3D network of cells forms a breast cancer tumor.

18. The method of claim 17, wherein the breast cancer cells comprise human breast cancer epithelial cells and wherein the non-cancerous breast tissue cells comprise human breast fibroblasts.

19. The method of claim 14, further comprising detecting toxicity of the cancer therapeutic compound as measured by histological, biochemical, physiological changes, or a combination thererof, of the cell network.

20. The method of claim 14, wherein the cancer cells are breast cancer cells.

21. The method of claim 14, wherein the network of cells includes breast cancer cells and non-cancerous breast tissue cells.

22. The method of claim 21, wherein the breast cancer tumor cells form a spheroid.

23. The method of claim 14, further comprising placing the cancer tissue construct in a tissue chamber configured to house the tissue construct such that the tissue construct forms a barrier between upstream and downstream flow of media through the chamber directing flow of media through the channels of the tissue construct, wherein the chamber has at least one input portal upstream of the location of the tissue construct and at least one output portal downstream of the location of the tissue construct, wherein the tissue chamber is coupled to at least one pump to control flow of media through the tissue chamber.

* * * * *